United States Patent [19]

Webster et al.

[11] Patent Number: 5,965,531
[45] Date of Patent: Oct. 12, 1999

[54] METHOD OF REDUCING PERIVASCULAR LESIONS USING INSULIN-LIKE GROWTH FACTOR I

[75] Inventors: Henry de Forest Webster, Chevy Chase, Md.; Samuel Komoly, Budapest, Hungary; Da-Lin Yao, Germantown, Md.; Xia Liu, Ossning, N.Y.; Lynn D. Hudson, Bethesda, Md.

[73] Assignee: National Institutes of Health, Rockville, Md.

[21] Appl. No.: 08/705,820

[22] Filed: Aug. 30, 1996

Related U.S. Application Data

[60] Provisional application No. 60/003,055, Aug. 31, 1995, and provisional application No. 60/021,060, Jul. 2, 1996.

[51] Int. Cl.$^6$ .................................................. A61K 38/00
[52] U.S. Cl. .................................. 514/12; 514/3; 514/21; 530/303
[58] Field of Search ................................. 514/12, 21, 3; 530/303

[56] References Cited

U.S. PATENT DOCUMENTS

| 5,565,428 | 10/1996 | Clark et al. | 514/12 |
| 5,861,373 | 1/1999 | Gluckman et al. | 514/3 |

FOREIGN PATENT DOCUMENTS

| WO93/02695 | 2/1993 | WIPO . |
| 9310806 | 10/1993 | WIPO . |

OTHER PUBLICATIONS

HCAPLUS DN 123:133926, Maack et al., WO 95/13823. abstract, 1995.
BIOSIS DN 98381557, Yao et al., *Proced: of the Nat. Acad. of Sci. of the USA*, 92(13), 6190–4 (abstract), 1995.
BIOSIS DN 98299307, Liu et al., 47th Annual Meeting of the Am. Acad. of Neurology 1995. *Neurology* 45 (4 Suppl. 4) A225, 1995.
Liu et al., *Multiple Sclerosis*, vol. 1, pp. 2–9, Apr. 1995.
"NIH research suggests IGF–I as treatment for MS", *Biotechnology News*, (Mar. 29, 1996) vol. 16, No. 8, p. 3.
Gehrmann et al, "Expression of Insulin–like Growth Factor–I and Related Peptides during Motoneuron Regeneration", *Experimental Neurology*, (1994) vol. 128, pp. 1–9.
Komoly et al, "Insulin–like growth factor I gene expression is induced in astrocytes during experimental demyelination", *Proc. Natl. Acad. Sci. USA*, (Mar. 1992), vol. 89, pp. 1894–1998.
Liu et al., "Astrocytes Express Insulin–like Growth Factor–I (IGF–I) and Its Binding Protein IGFBP–2, during Demyelination Induced by Experimental Autoimmune Encephalomyelitis", *Molecular and Cellular Neurosciences*, (1994) vol. 5, pp. 418–430.
Liu et al, "Insulin–like growth factor I treatment reduces clinical deficits and lesion severity in acute demyelinating experimental autoimmune encephalomyelitis", *Multiple Sclerosis*, (1995) vol. 1, pp. 2–9.
Webster, "Myelin Injury and Repair", *Advances in Neurology*, (1993) vol. 59, pp. 67–73.
Webster, "Growth factors and myelin regeneration in Multiple Sclerosis", *Multiple Sclerosis*, (1997) vol. 3, pp. 1–8.
Yao et al., "Insulin–like growth factor I treatment reduces demyelination and up–regulates gene expression of myelin–related proteins in experimental autoimmune encephalomyelitis", *Proc. Natl. Acad. Sci. USA* (Jun. 1995) vol. 92, pp. 6190–6194.
Yao et al, "Cryogenic Spinal Cord Injury Induces Astrocytic Gene Expression of Insulin–Like Growth Factor I and Insulin–Like Growth Factor Binding Protein 2 During Myelin Regeneration", *Journal of Neuroscience Research*, (1995) vol. 40, pp. 647–659.
Komoly et al., Society for Neuroscience—Abstract, 1991.
Yao et al., Society for Neuroscience—Abstract, 1992.
Yao et al., American Association of Neuropathologists—Abstract, 1992.
Webster et al., American Association of Neuropathologists—Abstract, 1993.
Komoly et al., International Symposium on Neural Regeneration, Asilomar, CA—Abstract, 1991.
Yao et al., The Fifth International Symposium on Neural Regeneration, Asilomar, CA—Abstract, 1993.
Yao et al., American Society of Neurochemistry—Abstract, 1995.
The IFNB Multiple Sclerosis Study Group, "Interferon beta–1b in the treatment of multiple sclerosis" *Neurology* 45:1277–1285 (1995).
Filippi et al., "Quantitative brain MRI lesion load predicts the course of clinically isolated syndromes suggestive of multiple sclerosis" *Neurology* 44:635–641 (1994).
Beck et al., "Igf1 Gene Disruption Results in Reduced Brain Size, CNS Hypomyelination, and Loss of Hippocampal Granule and Striatal Parvalbumin–Containing Neurons" *Neuron*, 14:717–730 (1995).
Carson et al., "Insulin–like Growth Factor I Increases Brain Growth and Central Nervous System Myelination in Transgenic Mice" *Neuron*, 10:729–740 (1993).

(List continued on next page.)

*Primary Examiner*—Johann Richter
*Assistant Examiner*—C. Delacroix-Muirheid
*Attorney, Agent, or Firm*—William J. McNichol, Jr.; Reed Smith Shaw & McClay LLP

[57] ABSTRACT

A disease or disorder associated with myelin injury, such as multiple sclerosis, is treated by administering to a patient in need thereof an effective amount of insulin-like growth factor I (IGF-I). The method reduces blood brain and blood nerve barrier permeability defects. It also decreases the size and number of perivascular lesions (often associated with myelin breakdown) and reduces the formation of sclerotic plaques in the central nervous system. IGF-I administration also reverses the clinical deficits associated with myelin injury, including visual defects, unsteadiness, poor coordination, muscular weakness and paralysis.

16 Claims, 26 Drawing Sheets

OTHER PUBLICATIONS

Lee et al., "Ischemic Injury Induces Brain Glucose Transporter Gene Expression" *Endocrinology,* 133(6):2540–2544 (1993).

Mathews et al., "Growth Enhancement of Transgenic Mice Expressing Human Insulin–Like Growth Factor I" *Endocrinology,* 123(6):2827–2833 (1988).

Yao et al., "Insulin–like Growth Factor I Given Subcutaneously Reduces Clinical Deficits, Decreases Lesion Severity and Upregulates Synthesis of Myelin Proteins in Experimental Autoimmune Encephalomyelitis" *Life Sciences,* 58(16):1301–1306 (1996).

Stone et al., "The Effect of Interferon–β on Blood–Brain Barrier Disruptions Demonstrated by Contrast–enhanced Magnetic Resonance Imaging in Relapsing–Remitting Multiple Sclerosis" *Ann. Neurol.* 37:611–619 (1995).

Bondy et al., Ontogeny and Cellular Distribution of Brain Glucose Transporter Gene Expression *Molecular and Cellular Neurosciences* 3:305–314 (1992).

Bondy et al., "Clinical Uses of Insulin–like Growth Factor I" *Annals of Internal Medicine,* 120(7):593–601 (1994).

Stong et al., "Effects of Multiple Subcutaneous Doses of rhIGF–1 on Total and Free IGF–1 Levels of Blood Glucose in Humans" *Annals New York Academy of Sciences* 692:317–320 (1993).

Clark et al., "Insulin–like Growth Factor–1 Stimulation of Lymphopoiesis" *J. Clin. Invest.* 92:540–548 (1993).

Robbins et al., "Immunological effects of insulin–like growth factor–I — enhancement of immunoglobulin synthesis" *Clin. Exp. Immunol.* 95:337–342 (1994).

Hartung, "Pathogenesis of inflammatory demyelination: implications for therapy" *Current Opinion in Neurology* 8:191–199 (1995).

Polman et al., "The treatment of multiple sclerosis: current and future" *Current Opinion in Neurology* 8:200–209 (1995).

Paty et al., "Interferon beta–1b is effective in relapsing–remitting multiple sclerosis" *Neurology* 43:662–667 (1993).

Paty, "Magnetic resonance in multiple sclerosis" *Current Opinion in Neurology and Neurosurgery* 6:202–208 (1993).

Grossman, "Magnetization Transfer in Multiple Sclerosis" *Ann. Neurol.* 36:S97–S99 (1994).

Miller, "Magnetic Resonance in Monitoring the Treatment of Multiple Sclerosis" *Ann. Neurol.* 36:S91–S94 (1994).

Husted, "Contributions of neuroimaging to diagnosis and monitoring of multiple sclerosis" *Current Opinion in Neurology* 7:234–241 (1994).

Armstrong et al., "In Vitro Analysis of the Oligodendrocyte Lineage in Mice during Demyelination and Remyelination" *The Journal of Cell Biology* 111:1183–1195 (1990).

Ballotti et al., "Insulin–like growth factor I in cultured rat astrocytes: expression of the gene, and receptor tyrosine kinase" *EMBO Journal* 6(12):3633–3639 (1987).

Behar et al., "Growth and Differentiation Properties of O–2A Progenitors Purified From Rat Cerebral Hemispheres" *Journal of Neuroscience Research* 21:168–180 (1988).

Carson et al., "Myelin and 2',3'–Cyclic Nucleotide 3'–Phosphohydrolase Levels are Elevated in Transgenic Mice Producing Increased Levels of Insulin–like Growth Factor–1 (IGF–1)" *Transactions of the American Society for Neurochemistry* 19(1):82 (1988).

Carson et al., "Myelin Content Increased in Transgenic Mice Producing Elevated Levels of Insulin–like Growth Factor–1 (IGF–1)" *Neuroscience Absts.* 14:119 (1988).

Palmiter et al., "Hypomyelination Caused by Growth Hormone Deficiency is Reversed by Insulin–like Growth Factor 1 in Transgenic Mice" *Transactions of the American Society for Neurochemistry* 20(1):286 (1989).

Morel et al., "Formation, Structure, and Biochemistry of Myelin" *Basic Neurochemistry: Molecular, Cellular, and Medical Aspects,* 4th Ed. New York, 1989; pp. 109–136.

Mozell et al., "Insulin–like Growth Factor I Increases Myelin Synthesis in Rat Brain Aggregate Cultures" *Transactions Of The American Society For Neurochemistry* 19(1):83(1988).

Mozell et al., "Insulin–like Growth Factor–I Stimulates Regeneration of Oligodendrocytes In Vitro" *Annals of the New York Academy of Sciences* 540:430–432 (1988).

Raine, "Neurocellular Anatomy" *Basic Neurochemistry: Molecular, Cellular, and Medical Aspects,* 4th Ed. New York, 1989; pp. 3–33.

Rechler, "The Nature and Regulation of the Receptors For Insulin–like Growth Factors" *Ann. Rev. Physiol.* 47:425–442 (1985).

Rosenberg et al., "Hundred–fold increase in neuronal vulnerability to glutamate toxicity in astrocyte–poor cultures of rat cerebral cortex" *Neuroscience Letters* 103:162–168 (1989).

Sara et al., "Characterization of somatomedins from human fetal brain: Identification of a variant form of insulin–like growth factor I" *Proc. Natl. Acad. Sci. USA* 83:4904–4907 (1986).

Shemer et al., "Insulin–like Growth Factor I Receptors in Neuronal and Glial Cells" *The Journal of Biological Chemistry* 262(16) :7693–7699 (1987).

Silver, "Transplantation Strategies Using Embryonic Astroglial Cells to Promote CNS Axon Regeneration in Neonatal and Adult Mammals" *Clinical Research* 36:196–199 (1988).

Torres–Aleman et al., "Trophic Effects of Insulin–like Growth Factor–I on Fetal Rat Hypothalamic Cells in Culture" *Neuroscience* 35(3):601–608 (1990).

van der Pal et al., "Effects of Insulin and Insulin–like Growth Factor (IGF–1) on Oligodendrocyte–Enriched Glial Cultures" 19:483–490 (1988).

Werner et al., "The Insulin–like Growth Factor I Receptor: Molecular Biology, Heterogeneity, and Regulation" *Insulin–like Growth Factors: Molecular and Cellular Aspects,* Ed. D. LeRoith, CRC Press, Boca Raton, 1991; 16–47.

Yamaguchi et al., "Increase of extracellular insulin–like growth factor I (IGF–I) concentration following electrolytical lesion in rat hippocampus" *Neuroscience Letters* 128:273–276 (1991).

McMorris, "Cyclic AMP Induction of the Myelin Enzyme 2', 3'–Cyclic Nucleotide 3'–Phosphohydrolase in Rat Oligodendrocytes" *Journal of Neurochemistry* 41:506–515 (1983).

COMPARISON OF BEHAVIORAL SEVERITY

LOW DOSE (0.2 mg/rat/day) (n=8)

HIGH DOSE (1 mg/rat/day) (n=11)

COMPARISON OF BODY WEIGHT

A

B

METHOD OF REDUCING PERIVASCULAR LESIONS USING INSULIN-LIKE GROWTH FACTOR I

This application derives priority from a provisional patent application, Ser. No. 60/003,055, which was filed on Aug. 31, 1995 which claims the benefit of provisional application Ser. No. 60/021,060 filed Jul. 2, 1996.

BACKGROUND OF THE INVENTION

FIELD OF THE INVENTION

The present invention relates to a method for preventing and/or reducing and/or eliminating perivascular lesions by the administration of insulin-like growth factors.

BACKGROUND OF THE INVENTION

Neurons communicate with one another by sending electrical impulses along cellular processes called axons; these processes are insulated with a protein-lipid composite substance called myelin. Myelin is produced by specialized cells (generically referred to as glial cells, or glia). In the central nervous system (CNS, i.e. the brain and spinal cord), the myelin producing glia are called oligodendrocytes, while in the peripheral nervous system the myelin-producing glia are called Schwann cells. In both cases, the myelin sheath is not continuous, but consists of segments of myelin approximately 1 millimeter in length separated by 0.5–1.5 micrometer gaps called nodes of Ranvier. These periodic gaps in the myelin sheath are important in the propagation of electrical signals down the axon.

During CNS development, an oligodendrocyte forms processes that ensheathe and myelinate many nearby axons. The lipids and proteins needed for myelin growth, maintenance, and regeneration are synthesized in the cell body (the soma) of the oligodendrocyte and are transported along microtubules in thin processes that terminate at the outer, inner, and paranodal margins of each myelin segment (Webster, H. de F. (1993) Adv. Neurol. 59:67–73; See also FIG. 1). These myelin segments are compact membrane spirals. In the CNS, the outer surface of the myelin sheath contacts other myelin sheaths, surface membranes of other glial cells and neurons, or the extracellular compartment (FIG. 2). Peripheral myelin sheaths are formed by Schwann cells located in ganglia, roots and nerves.

Central myelin sheaths are vulnerable to severe injury because: (a) oxygen metabolites, lipid mediators, toxins, viruses, inflammatory cells, cytokines, and other substances can interact directly with myelin sheath surfaces; (b) the amount of myelin membrane maintained by each oligodendrocyte is large; and (c) the thin glial processes that transport substances required for sheath maintenance probably also are easily damaged. Injury to the myelin sheaths may interrupt transport and produce myelin breakdown. Demyelination also occurs when axons are injured or transected, a process called "Wallerian degeneration."

When myelin sheaths or oligodendrocytes sustain injury, entire segments of myelin degenerate, and their remnants are phagocytosed by macrophages and to a much lesser degree by astrocytes. This process is called "primary demyelination" if most axons remain uninjured and is characteristic of the myelin breakdown seen in multiple sclerosis, experimental autoimmune encephalomyelitis (EAE), and progressive multifocal leukoencephalopathy. "Secondary demyelination" is defined as degeneration of myelin secondary to axonal disease; two well characterized examples include Wallerian degeneration and axonal degeneration ("dying back phenomenon"). In addition, degeneration of myelinated fibers may be secondary to destruction of dorsal root ganglion neurons.

Acute and chronic diseases associated with myelin injury in the CNS include multiple sclerosis (which is characterized at various stages as acute, relapsing-remitting, primary-progressive, secondary-progressive), neuromyelitis optica, optic neuritis, acute encephalomyelitis (which can be post-infectious or post-exanthem) and cervical myelopathy (which can be associated with infectious, connective tissue disease, transverse myelitis or autoimmune etiologies). Other diseases associated with CNS myelin degeneration including the leukodystrophies and progressive multifocal leukoencephalopathy.

Acute and chronic diseases associated with myelin injury in the peripheral nervous system (PNS) include acute inflammatory polyneuropathy, acute autoimmune neuropathy, Guillain Barre syndrome (GBS), recurrent and relapsing polyneuropathy, chronic inflammatory demyelinating polyneuropathy (CIDP), paraneoplastic syndromes, diabetes mellitus, connective tissue disease (e.g., vasculitis, systemic lupus erythematosus), and neuropathies associated with autoimmune diseases, cancer and infections caused by retroviruses, viruses and other infectious agents.

There are other inflammatory (presumably autoimmune) disorders affecting both the CNS and PNS which are associated with perivascular lesions with mononuclear inflammatory infiltrates and abnormalities of white matter (myelinated nerve fibers). For example, Sjogren's syndrome (SS) is an autoimmune disorder which affects approximately 3% of the adult population. Conservatively, approximately 25% of SS patients develop neurologic complications affecting the CNS and the PNS (i.e., dorsal root ganglia, spinal nerve roots and peripheral nerves of the sensory, motor and autonomic systems). SS is an example of an inflammatory neurological disorder in which the blood brain and blood nerve barrier of small vessels are compromised and are unable to prevent trafficking of mononuclear cells across the vascular endothelium into the perivascular space and nervous system tissue.

Mononuclear infiltrates of the small blood vessels of the central nervous system are a prominent and ubiquitous feature of SS. Although the organization and function of the white matter (myelinated fibers) is abnormal in SS, frank demyelination (with plaque formation) of the histopathologic type observed in Multiple Sclerosis (MS) is not present. The perivascular, mononuclear cells synthesize cytokines and excitatory neurotoxins which damage the surrounding nervous system. Perivascular inflammatory infiltrates containing mononuclear cells also occur in idiopathic polymyositis, a disorder of the musculoskeletal system which is thought to be immune-mediated.

MS, which is limited to the CNS, has all of the foregoing clinical and histopathological manifestations of SS but is also characterized by demyelination and gliosis (scarring). MS affects 350,000 Americans and is, with the exception of trauma, the most frequent cause of neurologic disability in early to middle adulthood. Indirect evidence supports an autoimmune etiology for MS, perhaps triggered by a viral infection in a genetically susceptible host. As in other chronic inflammatory disorders, the manifestations of MS are variable and range from a benign illness to a rapidly evolving and incapacitating disease. Complications from MS may affect multiple body systems and may require profound adjustments in lifestyle and goals for patients and their families.

MS derives its name from the multiple scarred areas visible on macroscopic examination of the brain. These demyelinating lesions, termed plaques, are well-demarcated gray or pink areas easily distinguished from surrounding white matter. Demyelinating lesions are historical evidence of the occurrence of or the continued presence of perivascular lesions. Occasionally, plaques are also present in gray matter (neuron cell bodies). Plaques vary in size from 1 or 2 millimeters to several centimeters. The MS lesion is defined as including both perivascular and demyelinating lesions. The acute MS lesion, occasionally found on autopsy, is characterized by increased permeability of the blood brain barrier, perivascular cuffing and tissue infiltration by mononuclear cells, predominantly T lymphocytes and macrophages, and by demyelination. B cells and plasma cells are rarely found. The inflammatory infiltrates appear to mediate the loss of myelin sheaths that surround axon cylinders. As the lesion progresses, large numbers of macrophages and microglial cells, (specialized CNS phagocytes of bone marrow origin) scavenge the myelin debris, and proliferation of astrocytes (gliosis) occurs. Proliferation of oligodendrocytes is also present initially, but these cells appear to be destroyed as the infiltration and gliosis progress. Gliosis is more severe in MS lesions than in most other neuropathologic conditions. In chronic MS lesions, complete or nearly complete demyelination, dense gliosis, and loss of oligodendrocytes are present.

MS lesions as detected by neuroimaging techniques and/or histopathology are typically more numerous than anticipated on the basis of clinical criteria. Selective demyelination with sparing of axon cylinders is the hallmark of the disease, yet partial or total axonal destruction, and in extreme cases cavitation, may occur. Although partial remyelination (shadow plaques) is occasionally present, in most lesions significant remyelination does not occur.

Viral infection of neurons and glial cells may also produce demyelinating lesions. Severe white matter lesions are present in subacute sclerosing panencephalitis, caused by measles virus, and in progressive multifocal leukoencephalopathy, a frequently fatal JC virus of the CNS. (Johnson, R. T. *Viral Infections of the Nervous System,* 1982, Raven Press, New York). In addition to the well known neuronal lesions, herpes virus infections may also produce primary demyelinating lesions. Multifocal demyelinating lesions were found in the optic nerves, brain, and spinal cord during experimental infection with herpes virus type 2 (HSV-2) (Martin, J. R. (1982) *J. Neuropathl. Exp. Neurol.,* 41:253–266; Martin, J. R. et al. (1982) *Br. J. Exp. Pathol.* 63:651–666). Remyelination occurred, and the topographic distribution of spinal cord lesions was not tract associated. Instead, it resembled that seen in some cases of MS (Flynn, T. E. et al. (1983) *J. Neurol. Sci.* 61:327–339). Axons in early demyelinating lesions were found to contain a few nucleocapsids and viral particles, and it was proposed that neuronal infection and axonal transport of virus could lead to foci of oligodendrocyte infection and primary demyelination remote from sites of neuronal infection. (FIG. 3) (Martin, J. R. (1984) *J. Neurol. Sci.* 63:63–74; Martin, J. R. et al. (1988) in: A multidisciplinary approach to myelin disease. New York: Plenum Press; 329–340).

Examination of fresh MS lesions has shown that there are numerous oligodendrocyte-like cells and possible precursors with immunoreactivity for myelin-related enzymes, proteins, and glycolipids (Prineas, J. W. et al. (1989) *Lab Invest.* 61:489–503). In more chronic active and in inactive lesions, similar cells and regenerating sheaths are much less frequent, suggesting that the capacity for oligodendrocytes to proliferate, ensheathe demyelinated axons, and regenerate myelin is reduced during progression of demyelination. In subacute and chronic spinal cord lesions, there may be substantial numbers of regenerated sheaths produced by Schwann cells (Itoyama, Y. et al. (1983) *Ann. Neurol.* 14:339–346; Itoyama et al. (1985) *Acta Neuropathol.,* 65:217–223); astrocytes are also thought to play an important role in the remyelination process.

Immunosuppressive drugs have been the cornerstone of MS therapy, although their efficacy is limited and their chronic use entails considerable risk. Long a mainstay of MS therapy, adrenocorticotropic hormone and glucocorticoids are used for their anti-edema and anti-inflammatory effects. Pulse therapy with these agents speeds the tempo of recovery from acute attacks and may modestly improve the degree of recovery that occurs. They are useful as short-term therapy for relapsing MS. There is no evidence that their use alters the long-term course of the disease.

More aggressive therapies have been employed in attempts to limit the number or severity of relapses in relapsing MS or halt chronic progressive MS in patients with rapid neurologic deterioration. The chronic use of glucocorticoids has not proved useful in the treatment of MS, although clinical trials have employed only low dosages. The antimetabolite, azathioprine, given orally on an outpatient basis is a relatively safe and well-tolerated form of chronic immunosuppression. Its beneficial effect is modest in controlled trials and must be weighed against potential risks that include hepatitis, susceptibility to infection, and a possible increased cancer risk. Pulse therapy with the alkylating agent cyclophosphamide is of benefit to young (<40 years) ambulatory patients with rapidly progressing MS. The side effects associated with treatment are considerable and include nausea, hair loss, a risk of hemorrhagic cystitis, and temporary profound immunosuppression. A modest effect of cyclosporin on the course of chronic progressive MS is also present, but side effects, notably hypertension and reversible renal dysfunction, have limited its widespread use.

More than 100 other therapies have been proposed for treatment of MS, most recently treatment with gamma-interferon. Interferon beta-1b is currently being utilized in the treatment of relapsing-remitting MS. (See, for example, The IFNB Multiple Sclerosis Study Group, et al. (1995) *Neurology* 45:1277–1285). Most represent variants of non-specific immunosuppression strategies. Conversely, others have attempted to stimulate immunity on the assumption that MS may be caused by a chronic viral infection.

In cuprizone-induced demyelination, an experimental demyelination syndrome, hypertrophic astrocytes in lesions have been reported to produce insulin-like growth factor I (IGF-I) mRNA and protein. Regeneration of myelin began when cuprizone treatment stopped, and early in recovery oligodendrocyte precursors expressed the receptor for IGF-I, a finding that strongly suggests that IGF-I functions in the metabolism of oligodendrocytes and myelin in vivo (Komoly, S. et al. (1992) *Proc. Natl. Acad. Sci. USA* 89:1894–1898).

Astrocytes also produce IGF-I mRNA and protein during in vivo myelin regeneration in EAE (Liu et al (1994) *Md. Cell. Neurosci.* 5:418–430) and experimental spinal cord injury (Yao et al (1995) *J. Neurosci. Res.* 40:647–659).

In vitro, IGF-I enhances oligodendrocyte survival and stimulates expression of genes encoding myelin-basic protein (McMorris, F. A. et al. (1988) *J. Neurosci. Res.* 21:199–209; McMorris, F. A. et al. (1986) *Proc. Natl. Acad.*

Sci. USA 83:822–826). In vivo, IGF-I knockout mice (Beck, K. D. et al. (1995) Neuron, 14:717–730) and IGF-I transgenic mice (Carson, M. J. et al. (1993) Neuron 10:729–740; Mathews, L. S. et al. (1988) Endocrinology 123:2827–2833) further illustrate the crucial role of IGF-I in oligodendrocyte survival and function (i.e., myelination).

IGF-I is highly conserved across mammalian species. For example, there are only minor differences between the amino acid sequences of rat and human IGF-I; the observed differences between rat and human IGF-I are relatively few and mostly conserved in nature (i.e., a proline for aspartic acid at position B20, an isoleucine for serine at position C35, and a threonine for alanine at position D67). There are no differences between bovine, porcine and human IGF-I (Daughaday, W. H. and Rotwein, P. (1989) Endo. Rev. 10(1):68–91). As such, and beneficially, those in the art have utilized recombinant human IGF-I (rhIGF-I) for in vivo investigations in animal models, including mice and rats, indicating the highly conserved nature of the protein and its receptor.

rhIGF-I has been safely administered to healthy volunteers and was well tolerated (Stong, D et al (1993) Ann. N.Y. Acad. Sci. 692:317–320).

SUMMARY OF THE INVENTION

In the present invention, we disclose a novel method for reducing perivascular lesions, most preferably using insulin-like growth factor I (IGF-I). Typically, but not always, perivascular lesions occur after or during: brain or spinal cord trauma; ischaemic injury or insult; a spectrum of inflammatory conditions affecting the musculo-skeletal system, the peripheral nervous system and/or central nervous system; and autoimmune disorders such as MS. We disclose that administration of IGF-I in animals evidencing (1) disruption of the blood brain barrier; (2) perivascular lesions; and (3) behavioral deficits, beneficially and unexpectedly (1) decreases the permeability of the affected blood brain barrier; (2) reduces the size and/or number of the perivascular lesions; and (3) reduces the severity of and accelerates the recovery from such behavioral deficits.

With the foregoing disclosures, advantages and features of the invention that will become hereinafter apparent, the elucidation of the invention will be enhanced by reference to the following detailed description of the preferred embodiments of the invention and to the appended claims.

BRIEF DESCRIPTION OF THE FIGURES AND THE DRAWINGS

FIG. 1: Developing (left) and mature (right) oligodendrocytes shown with their processes and myelin sheaths, which are compact, spiral extensions of their surface membranes. In the developing and remyelinating cell (left), relatively small areas of the spiral are compact. Processes of the mature oligodendrocyte (right) extend to many myelin sheaths and are continuous with the thin belt of cytoplasm that surrounds the large area of compact adult myelin. This cytoplasmic belt includes an oligodendrocyte's outer tongue processes, its paranodal (lateral) loops, and its inner (periaxonal) tongue processes.

FIG. 2: Electron micrograph of transversely sectioned myelinated CNS axons. Alternating dense and less-dense lines of compact myelin are shown with inner (it) and outer (ot) tongue processes of oligodendrocytes. X180,000.

FIG. 3: Model for amplification of white matter infection and demyelination by cell to cell virus spread from infected neurons to oligodendrocytes. Proposed amplification factors are (a) multiplicity of oligodendrocytes providing myelin internodes to each axon (center arrow), (b) secondary spread between oligodendrocytes in glial columns (left arrows), and (c) loss of several internodes for each oligodendrocyte destroyed (right arrow).

FIG. 4: Number of exercise wheel rotations per 2 min period (mean±s.e.) after 8 days of placebo or IGF-I treatment. ***$P<0.0001$.

FIG. 5: Photographs of hind limb footprints after 8 days of placebo (A, B, and D, E), low (C), and high (F) doses of IGF-I. In the placebo-treated groups, dragging of hind limbs occurred in a few rats with very severe weakness; their hind limb stride length was zero (A and D). Even when weakness was mild, stride length of placebo-treated rats (B and E) was shorter than that of rats receiving low (C) and high (F) doses of IGF-I.

FIG. 6: Hind limb stride lengths of rats (mean±s.e.) after 8 days of placebo, low dose and high dose IGF-I treatment. *$P<0.05$; **$P<0.01$.

FIG. 7: (A–C) are photomicrographs of Evans blue-serum albumin fluorescence in longitudinal spinal cord sections from rats with EAE for 12 days (A) (just before treatment started) and 16 days (B and C). In B, areas of perivascular and parenchymal fluorescence are larger after 4 days of placebo treatment. When B and C are compared, perivascular areas of fluorescence are much smaller in C after 4 days of IGF-I treatment, 3.0 mg $kg^{-1}$ $day^{-1}$. (X100). (D–F) H&E stained longitudinal spinal cord sections from rats with EAE on day 12 and day 20. In D, (day 12, just before treatment started), there are more than six perivascular inflammatory lesions. In E, after 8 days of placebo treatment, the inflammatory lesions are much larger. In F, after 8 days of IGF-I, 3.0 mg $kg^{-1}$ $day^{-1}$ lesions are smaller and fewer than at 12 days and much less severe than after placebo treatment for 8 days (X80).

FIG. 8: Lesion numbers $mm^{-2}$ (mean±s.e.) in EAE at 12 days (just before treatment) and at 20 days, after 8 days of placebo or two dose levels of IGF-I treatment. *$P<0.05$, ***$P<0.0001$.

FIG. 9: Lesion areas $mm^{-2}$ of section area (mean±s.e.) at 12 days, before treatment started and at 20 days, after 8 days of placebo or two dose levels of IGF-I treatment. *$P<0.05$, ***$P<0.0001$.

FIG. 10: Scores of EAE clinical deficit severity (range, 0–5; mean±S.E.) during placebo and two dose levels of IGF-I treatment (see Example 1). *$P<0.05$; $P<0.01$; *$P<0.0001$.

FIG. 11: Body weight (mean±s.e.) during placebo and two dose levels of IGF-I treatment. * and ** represent P values of<0.05 and 0.01.

FIG. 12: Scores of clinical deficit severity (mean±S.E.) during treatment with placebo and s.c. IGF-I (A) or placebo and i.v. IGF-I (B). *$P<0.05$, **$P<0.01$.

FIG. 13: A: Number of exercise wheel rotations per 2 min period (mean±S.E.) after 8 d of either placebo or of IGF-I (s.c. or i.v.). **$P<0.01$. B: Hind limb stride lengths (mean±S.E.) after 8 d of placebo or IGF-I treatment (s.c. or i.v.). *$P<0.05$.

FIG. 14(A–B): Lesion numbers/$mm^2$ (A) and lesion areas/$mm^2$ (B) in EAE at 20 d after 8 d of placebo or IGF-I treatment (s.c. or i.v.). Values are means±S.E. *$P<0.05$, $P<0.01$, *$P<0.0001$.

FIG. 15(A–B): Autoradiographs of MBP mRNA densities and distributions after 20 d of EAE. In sections from placebo-treated rats (A,a,b), relative mRNA levels were greatly reduced in lesion areas (black arrows) and in non-lesion areas, they were lower than they were after IGF-I treatment (A,c,d). MBP mRNA levels were much higher in lesion areas after both s.c. and i.v. IGF-I treatment (compare white and black arrow areas in A,c,d and A,a,b). Relative MBP mRNA levels as % levels in sections from untreated controls (B) were significantly higher after both s.c. and i.v. IGF-I treatment ***P<0.0001, n=3 (s.c. IGF-I), n=5 (i.v. IGF-I).

FIG. 16: T lymphocyte proliferation observed when $10^2$–$10^{-7}$ μg/ml IGF-I is added to MBP-containing medium is not significantly different from that observed with MBP alone.

FIG. 17(A–D): Effect of IGF-I on clinical score (A,C) and body weight (B,D) when IGF-I administration begins at 4 days (A,B) or 1 day (C,D) after immunization with MBP-specific T-cells. *P<0.05; P<0.01; *P<0.001.

FIG. 18(A–D): Lesion number (A), lesion area (B), CD4-positive T cells (C) and α/β TCR-positive T cells (D) after 6 days of IGF-I treatment. *P<0.05.

FIG. 19(A–B): Distribution of ED-1-positive cells in spinal cord white and grey matter in IGF-I-treated (A) and placebo-treated (B) rats.

FIG. 20: ED-1 positive cells, after 6 days of IGF-I treatment.

FIG. 21: Levels of MBP mRNA as measured by in situ hybridization in and around EAE lesions after 6 days of IGF-I and placebo treatment.

FIG. 22(A–D): Autoradiogram, GT-1 mRNA expression in spinal cord of normal (A), EAE onset, 12 d, (B), EAE 20 d, after 8 d of placebo (C) or IGF-I (D) treatment.

FIG. 23(A–C): Autoradiogram of GT-1 mRNA expression in longitudinal sections of spinal cords from normal rats (A) and EAE rats after 20 d of placebo (B) or IGF-I treatment (C).

FIG. 24: On left, emulsion autoradiograms of GT-1 mRNA distribution in normal rat spinal cord (A), placebo-treated rat, EAE 20 d (B), and 20 d EAE after 8 d IGF-1 (C). On right, graph shows relative levels, GT-1 mRNA, 8 d of placebo or IGF-I.

FIG. 25(A–D): Spinal cord section, normal rat, double immunolabeled with anti- GT-1 (FITC) (A), and Factor VIII (Texas red, B), confirming endothelial localization of GT-1. Double labeling with GFAP and GT-1 shows more intense staining in placebo (C) than IGF-I-treated rats (D).

FIG. 26: Scores of clinical deficit severity (means, range 0=normal, 5=moribund) during chronic relapsing EAE (crEAE) induced in SJL mice by passive transfer of MBP sensitized T cells. IGF-I was given to IC Group, s.c., once daily (0.6 mg/kg) from days 7–16 after transfer. The Control Group (PC) received daily placebo injections on the same schedule (vehicle solution without IGF-I). IC vs. PC differences in maximum clinical scores were significant on day 10, 42 and 56 (*P≦0.05).

FIG. 27: Sixty three days after passive transfer (see FIG. 26), areas of inflammatory lesions and demyelinating lesions in longitudinal spinal cord sections were significantly less in the IGF-I treated mice (IC) than in those treated with placebo (*P<0.05).

DETAILED DESCRIPTION

Figure 1:
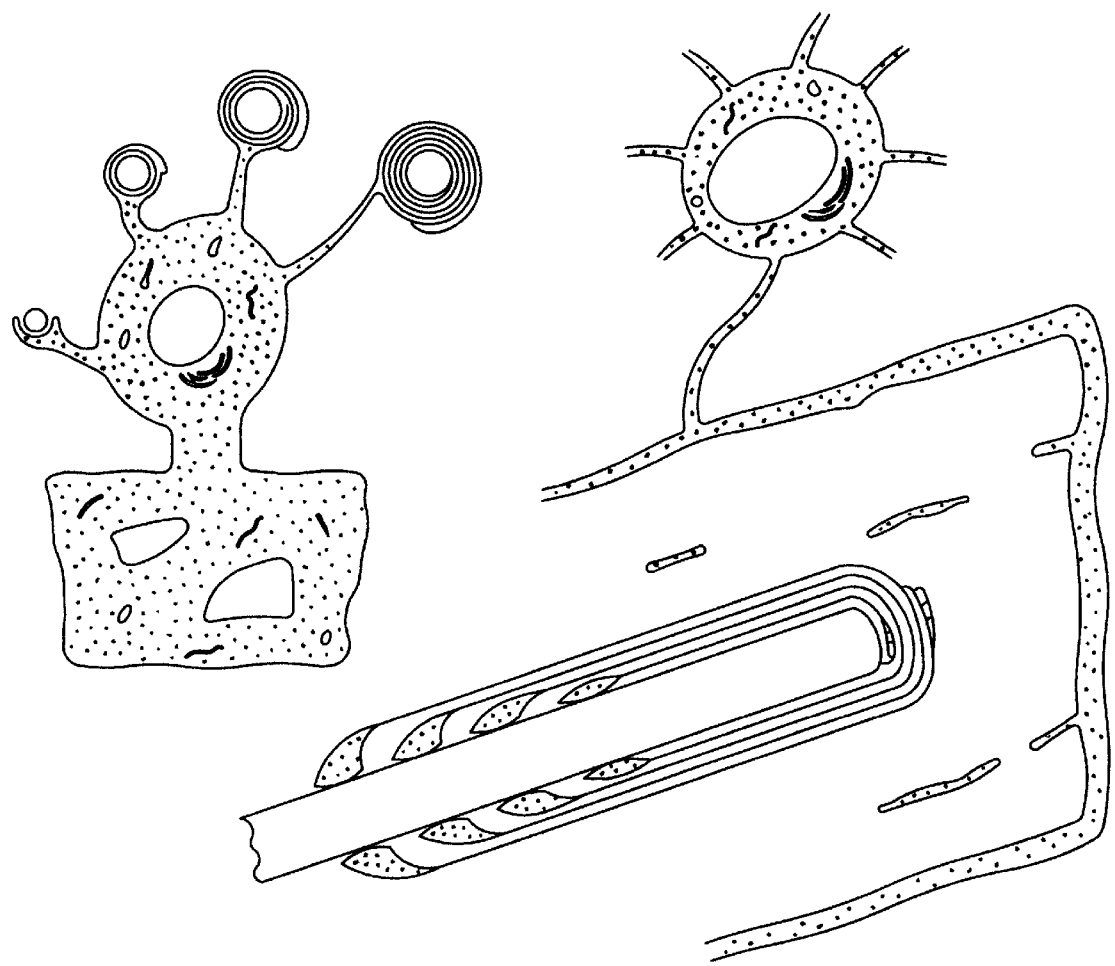
Figure 2:
Figure 3:
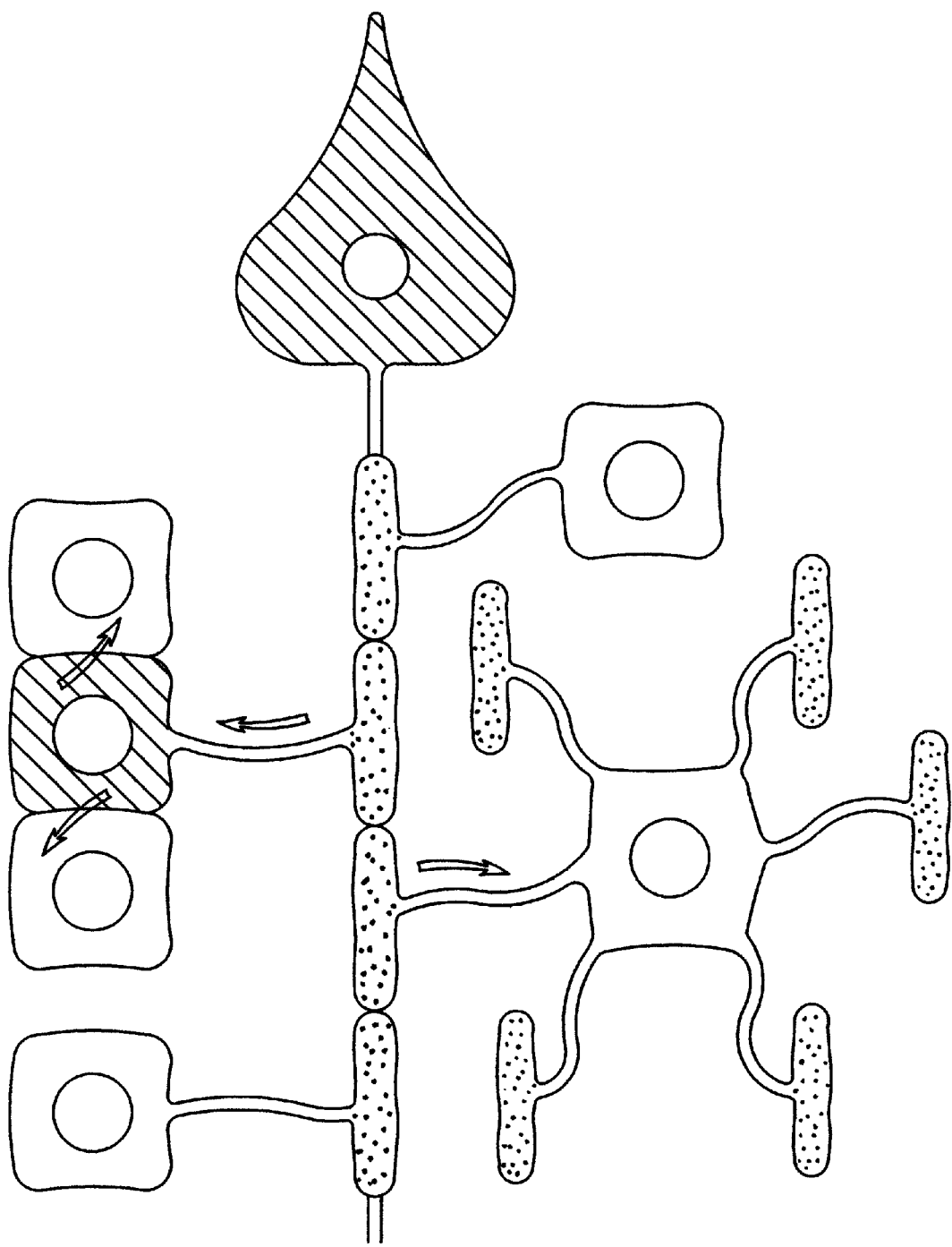

As used herein, the following terms have the following definitions and these definitions, to the extent that they may or do conflict with other definitions, control.

"Nervous system" means neurons, glia, and other supporting cells (e.g., Schwann, satellite) and the connective tissue layerings and coverings of neurons, glia, and other supporting cells.

"Central nervous system" or "CNS" means the nervous system of the brain and spinal cord.

"Peripheral nervous system" or "PNS" is the nervous system excluding the CNS.

"Blood brain barrier" or "BBB" is a selectively permeable, functional and physical barrier to the movement of cells and molecules into and out of the CNS via blood vessels.

"Blood nerve barrier" or "BNB" is a selectively permeable functional and physical barrier to the movement of cells and molecules into and out the PNS via blood vessels.

"Ganglia" means neuron cell bodies and their supporting cells; ganglia are localized in the PNS.

"Insulin-like growth factor-I" or "IGF-I" means a substantially purified and isolated 70 amino acid protein, preferably generated via recombinant DNA techniques, and having an affinity for the IGF-I receptor and further including derivatives having any substitutions and/or deletions and/or additions which do not eliminate the binding affinity for the IGF-I receptor. This definition includes $des_{1-3}$ IGF-I ("IGF-III") and may include IGF-II.

"Vascular lesions" are sites in vasculature and/or a blood vessel which have been compromised. "Compromise or compromised" mean increased or enhanced permeability; compromise and compromised can also include, but are necessarily limited to, a physical breach.

"Perivascular lesions" are sites near and/or adjacent to and/or surrounding and/or including vascular lesions which are typically, but not always, accompanied by accumulation of inflammatory leukocytes and/or fluid and/or damage to perivascular tissue.

"About" in reference to a numerical value means approximately +/–10% of the numerical value, e.g., "about 10%" means approximately 9 to 11%.

Presently, it is unclear how a perivascular lesion originates, whether the origin is by chemical, autoimmune, ischaemic, traumatic injury, infection, etc. However, regardless of the origin of the primary insult, the sequence of events leading to perivascular lesions begins with adhesion of leukocytes to vascular endothelium and reduced integrity of the blood-brain and/or blood-nerve barrier. There is typically recruitment of inflammatory leukocytes which traverse the vessel wall into the tissue and directly or indirectly (via secreted substances such as cytokines, chemokines, reactive oxygen intermediates, excitatory neurotoxins, etc.) induce increased vascular endothelial permeability and/or induce directly or indirectly toxic effects on the nervous system.

Thus, it is essential in such cases to reduce the abnormal permeability of the blood brain barrier and/or blood nerve barrier and/or blood vessels of the ganglia in an effort to mediate, prevent and/or reduce the above-described consequences associated with such perivascular lesions. For example, in order to effectively reduces the severity and treat a disease or disorder associated with a loss of myelin, associated with perivascular lesions, e.g., MS, it is essential to impact the perivascular lesions which lead to myelin loss.

This invention arose from our desire to provide a safe, effective treatment for diseases and disorders associated with perivascular lesions which may also lead to or result in myelin injury, for example, MS. Heretofore, the possibility of using IGF-I for the treatment of MS was suggested. However, our in vivo results demonstrate an overall rationale for the use of IGF-I in the treatment of diseases and disorders associated with perivascular lesions which may lead to or result in tissue injury. These results could not have been reasonably predicted based upon previous suggestions.

We have found that administration of insulin-like growth factor I effectively reduces the severity and/or promotes healing of perivascular lesions. Promotion of healing of those lesions includes reducing the number and/or the size of the lesions. Reducing the severity of these lesions includes the prevention of the formation of at least one new lesion and/or the prevention of at least one recurrent lesion and/or the prevention of the occurrence of at least one enlarging lesion. Such healing was incapable of prediction prior to our invention. By reducing or eliminating the perivascular lesions, partial or complete recovery or prevention of the deficits caused by such lesions is possible.

The method according to the invention is useful for reducing the severity and/or promoting the healing of perivascular lesions, which lesions may also lead to or result in myelin injury. Preferably, the disease is MS. However, the diseases and disorders discussed in the Background section are equally applicable to our invention.

Perivascular lesion size and/or number can be measured in vivo in a subject, such as a human, by the use of magnetic resonance imaging (MRI) analysis. Use of MRI allows for direct visualization of such abnormalities that is both objective and quantifiable. The use of MRI to detect and measure lesions in patients with MS is described in Paty, D. W and Li, D. K. B., "Interferon beta-1b is effective in relapsing-remitting multiple sclerosis. II. MRI analysis results of a multicenter, randomized, double-blind, placebo-controlled trial" (1993) *Neurology,* 43:662–667; Paty, D. W., "Magnetic resonance in multiple sclerosis" (1993) *Current Opinion in Neurology and Neurosurgery,* 6:202–208; Grossman, R. I., "Magnetization Transfer in Multiple Sclerosis" (1994) *Ann. Neurol.,* 36:S97–S99; Miller, D. H., "Magnetic Resonance in Monitoring the Treatment of Multiple Sclerosis" (1994) *Ann. Neurol.,* 36:S91–S94; Husted, C., "Contributions of neuroimaging to diagnosis and monitoring of multiple sclerosis" (1994) *Current Opinion in Neurology,* 7:234–241; the contents all of which are hereby incorporated by reference. Gadolinium enhanced MRI is preferred.

Generally, the number and/or size of perivascular lesions will be determined prior to initiation of treatment (i.e., "perivascular lesion baseline measurement"). The baseline measurement can be a single measurement or a series of measurements prior to initiation of treatment. The number and/or size of perivascular lesions is then periodically measured over the course of treatment (i.e., "perivascular lesion treatment measurement"). Generally, for purposes of comparing perivascular lesion treatment measurements with the baseline measurement to assess a reduction in the number and/or size of the lesions, the time between obtaining the baseline measurement and the treatment measurements is at least about six (6) months; this time period can, however, be in excess of six months. Stone, L. A. et al. (1995) *Annals of Neurology* 37:611–619, provides a general rationale for such timing with respect to Interferon-beta in relapsing-remitting MS.

One of the characteristics of such lesions is the natural tendency to decrease in number and size over time. For example, newly observed lesions have a tendency to grow in size for about four weeks, after which almost 60% will naturally fade away. A further 25% continue to fluctuate in size while only 16% become permanent and confluent with a neighboring lesion. Therefore, lesion activity can be assessed by, for example and not limitation, summing the area or volume of each measurable lesion to create an overall burden of disease (BOD) measurement. See, for example Charlish, P. "Unwrapping the riddle of multiple sclerosis." *Pharmaprojects Magazine,* June 1996, pp. 17–21, and Paty, D. W. et al "Interferon beta 1-b is effective in relapsing-remitting multiple sclerosis." *Neurology* 43(4):662 (1993).

Preferably, promotion of healing of perivascular lesions is assessed using comparative BOD measurements, e.g., determining a "baseline BOD measurement" (analogous to the above description) and a "treatment BOD measurement" (for example, and not limitation, at least about six months after initiation of treatment with IGF-I) and then obtaining a "BOD differential score" by comparing treatment BOD measurement with the baseline BOD measurement.

It is further noted that a reduction in the severity of perivascular lesions and/or promotion of the healing of perivascular lesions can be correlated with a decrease in the clinical evidence of disease caused by and/or which leads to perivascular lesions. For example and not limitation, in MS, it has been demonstrated that the risk of increased disability is dependent upon the number and size of lesions over time. (Filippi, M. et al. (1994) *Neurology* 44:635–641). Furthermore, a treatment which significantly prevents disease exacerbation in relapsing-remitting MS has been shown to reduce the overall perivascular lesion area, findings which were highly correlated with disease disability. (The IFNB Multiple Sclerosis Study Group, et al. (1995) *Neurology* 45:1277–1285).

Perivascular lesion activity as assessed by MRI can be, and preferably is, assessed by use of the following definitions: "new lesions" are lesions which have not previously been observed; "recurrent lesions" are lesions reappearing at the same site at which an earlier lesion had disappeared; "enlarging lesions" are those showing a significant increase in size from a previously stable-appearing lesion (significant can be defined as a change in size greater than 70% for a small (<1 cm) lesion, and greater than 10% for a large (>1 cm) lesion); and "activity event" is any new, recurrent or enlarging lesion. For the purposes of this disclosure, the foregoing definitions apply.

By reducing the likelihood of new lesion formation, or by decreasing the appearance of recurrent lesions, or by reducing the growth/size of enlarging lesions, i.e., by reducing or preventing an activity event, IGF-I beneficially inhibits the deleterious damage resulting to the CNS and/or the PNS by such lesions. This, then, decreases the overall impact to the, e.g., CNS by the underlying disease, e.g., MS.

Pharmaceutical salts of IGF-I suitable for administration by a variety of routes are known in the art and need not be described herein in detail. Examples of pharmaceutically acceptable salts of IGF-I and derivatives thereof according to the invention, include base salts, e.g., derived from an appropriate base, such as alkali metal (e.g., sodium), alkaline earth metal (e.g., magnesium), ammonium, and $NW_nH_m$ bases and salts wherein each of n and m are 0 to 4 and n+m is 4, and wherein W is a $(C_1-C_{18})$alkyl. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids.

Pharmaceutically-acceptable salts of a compound with a hydroxy group include, but are not limited to, the anion of the compound in combination with a suitable cation such as $Na^+$, and $NW_nH_m$, wherein W is a $(C_1-C_{18})$alkyl group, and n and m are 0 to 4, and n+m is 4.

A still further part of this invention is a pharmaceutical composition for treating or preventing diseases and disorders associated with perivascular lesions which lead to or result in myelin injury that comprises IGF-I and/or pharmaceutical salts thereof, and a pharmaceutically-acceptable carrier therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa. (1985).

For therapeutic use in a method of treating diseases and disorders associated with perivascular lesions which lead to or result in myelin injury, IGF-I, or its salt, can be conveniently administered in the form of a pharmaceutical composition containing IGF-I or its salt, and a pharmaceutically acceptable carrier therefor. Suitable carriers are well known in the art and vary with the desired form and mode of administration of the pharmaceutical composition. For example, they may include diluents or excipients such as fillers, binders, wetting agents, disintegrators, surface-active agents, lubricants, and the like. Typically, the carrier may be a solid, liquid, or vaporizable carrier, or combinations thereof. In one preferred embodiment, the composition is a therapeutic composition and the carrier is a pharmaceutically acceptable carrier.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

Each carrier must be "acceptable" in the sense of being compatible with the other ingredients in the formulation and not injurious to the patient. The carrier must be biologically acceptable and inert, i.e., it must permit the cell to conduct its metabolic reactions so that the compound of this invention may exert its therapeutic activity.

Formulations include those suitable for oral, rectal, nasal, topical (including buccal and sublingual), vaginal and parenteral (including subcutaneous, intramuscular, intravenous, intradermal, and transdermal) administration. Subcutaneous formulations, and formulations appropriate for oral administration, are preferred.

For example, to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of isotonicity adjusters such as sodium chloride, glucose or glycerin can be added to make the preparations isotonic. The aqueous sterile injection solutions may further contain anti-oxidants, buffers, bacteriostats, and like additions acceptable for parenteral formulations.

The formulations may conveniently be presented in unit dosage form and may be prepared by any method known in the art of pharmacy. Such methods include the step of bringing into association the active ingredient with the carrier which may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

IGF-I may be present in the composition in a broad proportion to the carrier. For instance, IGF-I may be present in the amount of 0.01 to 99.9 wt %, and more preferably in about 0.1 to 99 wt %. Still more preferably, IGF-I may be present in an amount of about 1 to 70 wt % of the composition.

The dosage of the IGF-I, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with other therapeutic agents, the incidence of side effects and the like.

In general, a dose suitable for application in the treatment of a disease or disorder such as MS is about 1.0 nanogram to about 1.0 gram/kg body weight/dose, preferably about 0.01 to 60 mg/kg body weight/dose, and still more preferably about 0.1 to 40 mg/kg body weight/dose per day.

The desired dose may be administered as 1 to 6 or more subdoses administered at appropriate intervals throughout the day. The desired dose may also be administered through a continuous release formulation. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 1.0 nanogram to about 1.0 gram/kg body weight/day. However, other amounts may also be administered.

IGF-I may be administered for therapy by any suitable route, including topical, oral, rectal, nasal, vaginal and parenteral (including intraperitoneal, subcutaneous, intramuscular, intravenous, intradermal, and transdermal) routes. IGF-I may also be administered by gene therapy whereby exogenous DNA encoding IGF-I is introduced into the patient, and expression of IGF-I protein occurs. Because gene therapy by definition contemplates administration of a gene which encodes a protein, and therapeutic treatment via the encoded protein, methods of administering IGF-I include IGF-I gene therapy. It will be appreciated that the preferred route will vary with the condition and age of the patient, the nature of the disorder and the chosen active ingredient including other therapeutic agents. Preferred is the subcutaneous route. However, other routes may also be utilized depending on the conditions of the patient and how long-lasting the treatment is.

While it is possible for IGF-I to be administered alone, it is preferably present as a pharmaceutical formulation. The formulations of the present invention comprise at least IGF-I, as defined above, together with one or more acceptable carriers thereof and optionally other therapeutic agents.

The method of the invention may be practiced by administration of IGF-I by itself or in combination with other active ingredients, including antiviral compounds, antiinflammatory compounds and/or other therapeutic agents in a pharmaceutical composition. Other therapeutic agents suitable for use herein are any drugs which are complementary to the action of IGF-I, whether effective by the same or a different mechanism. These include agents that are effective for the treatment of viral infections and/or associated conditions in humans, such as acyclovir, vidarabine, idoxuridine, trifluorothymidine, and foscarnet, among others. Also included are antiinflammatory agents, such as adrenocorticotropic hormone (ACTH) and glucocorticoids, and immunosuppressive agents, such as azathioprine, cyclophosphamide and cyclosporin.

The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

The following Examples are presented for the purpose of elucidation and not limitation.

EXAMPLE 1
IGF-I reduces lesion severity and behavioral deficits in EAE

Example 1 details the results of experiments designed to test the effects of IGF-I treatment on lesion severity in acute demyelinating EAE. Between 12 and 13 days after immunization with a spinal cord-containing emulsion, pairs of rats with the same degree of mild tail and hind limb weakness were given placebo or recombinant human IGF-I intravenously twice daily for 8 days. The results showed that IGF-I treatment reduced permeability defects in the BBB, decreased lesion severity and promoted behavioral recovery. To our knowledge, these are the first in vivo results evidencing the benefits derived from the use of IGF-I in a model of perivascular lesions.

Induction of EAE and IGF-I treatment

The emulsion used to induce EAE contained equal volumes of a suspension of guinea pig spinal cord in 0.9% saline (1 g ml$^{-1}$) and a suspension of 5 mg of *Mycobacterium tuberculosis* H37rv (American Type Tissue Culture Collection, Rockville, Md., USA) in 1 ml of complete Freund's adjuvant (DIFCO, Detroit, Mich., USA). While anesthetized, 100 adult male Lewis rats (250–300 g) received four intradermal injections of this emulsion: 0.1 ml in each hind footpad and 0.05 ml in each posterior nuchal region. Redness and moderate swelling of injected footpads was present for 7 days, declined and did not affect hind limb strength or gait during tests from 12–20 days.

Thirty rats were immunized for the first treatment trial. On day 12, when mild but definite weakness was first detected, eight pairs of rats with the same clinical scores were identified: eight rats were given 100 μg of recombinant human IGF-I (rhIGF-I) intravenously in the tail vein every 12 h for 8 days. The other eight rats received a placebo (same volume of sterile 0.89% saline) i.v. injection every 12 h for the same period. On day 20, after 8 days of placebo or IGF-I treatment, five pairs of rats were anesthetized and perfused before removing their spinal cords for histological study. Other segments of these spinal cords were cryoprotected and frozen. After anesthesia, some spinal cord segments from the other three pairs of rats were frozen before fixation. Other segments were embedded in paraffin and also studied histologically.

EAE was induced in 40 more rats and the same procedure was used for the second treatment trial. Eleven pairs of rats with the same deficit were selected and the IGF-I i.v. dose given twice daily was 500 μg instead of 100 μg. After 8 days of treatment, three pairs were given Evans-blue-bovine serum albumin (BSA) intravenously (see below) one hour before they were anesthetized. Then they were perfused along with five additional pairs of rats. After anesthesia, the spinal cords of the remaining three pairs were removed rapidly and frozen before fixation. Paraffin sections of these cords were also prepared; thus, sections from 11 pairs of rats were studied histologically and were used to count lesions and measure their areas.

Thirty rats were immunized for the third trial. On day 12, just before treatment began, six rats with the same mild definite clinical deficit were used to define BBB barrier changes (three rats) as well as lesion numbers and areas (all six rats). On day 12, 12 additional rats with the same degree of weakness were selected: six received 500 μg of IGF-I twice daily i.v. for 4 days. The other six received placebo injections. After 4 days of treatment three pairs received Evans blue-BSA 1 h before anesthesia and perfusion fixation. After deep anesthesia, spinal cords from the remaining three pairs of rats were removed rapidly, cryoprotected, and frozen. Frozen spinal cord segments from rats included in all three trials were stored for subsequent studies of oligodendrocyte function.

Examination

Weakness and gait defects associated with EAE from days 12–20 did not prevent normal eating and drinking. The rats were weighed and examined twice daily after day 10. Their hind footpads appeared normal and the severity of their clinical disease was graded from 1 to 5 as follows: (1) normal except for flaccid tail; (2) weakness of the tail and hind limbs, mild ataxia; (3) moderate paraparesis or severe ataxia; (4) some forelimb weakness, severe paraparesis, episodes of incontinence; (5) no hind limb movement, incontinence, impaired respiration. After training, gait, and limb strength were tested by placing each rat on an exercise wheel (diameter=24 cm) and counting the rotations made during a 2 min period of walking. Trained rats also were able to walk on a straight path which was 50–60 cm long. Hind feet were inked and footprints on poster paper provided measurements of stride length, which was reduced by weakness and was zero for the few placebo-treated rats with hind limb paralysis. Means and standard errors of rotation numbers and stride lengths were calculated and compared using Student t-tests with two tailed P values. Placebo and IGF-I-treated groups were considered to differ significantly when $P<0.05$. Before each injection, two observers determined clinical scores, weights, and test results independently without knowledge of previous results or treatment.

Blood-spinal cord barrier tests, tissue processing, and histology

The presence of lesions was verified based upon examination of the permeability of the BBB. We injected control and EAE rats i.v. with 3.5 ml kg$^{-1}$ of a 0.89% saline solution containing a mixture of 2% Evans blue and 10% BSA (Sigma) 1 h before they were anesthetized and perfused for 10 min. The perfusate was a solution of 4% 0.1M phosphate-buffered paraformaldehyde containing 15% picric acid (v/v)/ After overnight fixation at 4° C., spinal cords from normal control rats and from those with EAE for 12 days (onset of definite weakness, before treatment), 16 days (4 days of treatment), and 20 days (8 days of treatment) were cryoprotected and frozen. Cryostat sections mounted with Vectashield H-1000 mounting medium (Vector Laboratories, Burlingame, Calif., USA) were used to photograph areas of perivascular Evans blue-serum albumin fluorescence associated with lesions after 4 days of placebo and IGF-I treatment. Identical filtration and illumination methods were used. After covering the slide labels, fluorescence was measured using NIH Image Analysis 1.55 software. Comparable segments of spinal cords from normal controls and both EAE time points (12 days-before treatment, 8 days treatment with low and high IGF-I doses) were rinsed thoroughly in PBS, dehydrated and embedded in paraffin. Four non-overlapping longitudinal sections of these blocks were stained with hematoxylin and eosin (H&E) and examined. Slide labels were covered before Bioquant image analysis software was used to count lesions and measure their areas. Means and standard errors were calculated and used to determine if IGF-I treated rats differed significantly from placebo-treated rats. Paraffin-embedded blocks of brain, heart, liver, spleen kidney, and bladder from both groups also were sectioned, stained with H&E and examined light microscopically. All tests and procedures met NIH guidelines for the use of animals in research and the protocols for these experiments were approved by the NINDS Animal Care and Use Committee.

Gait, limb strength, and coordination

Figure 4:
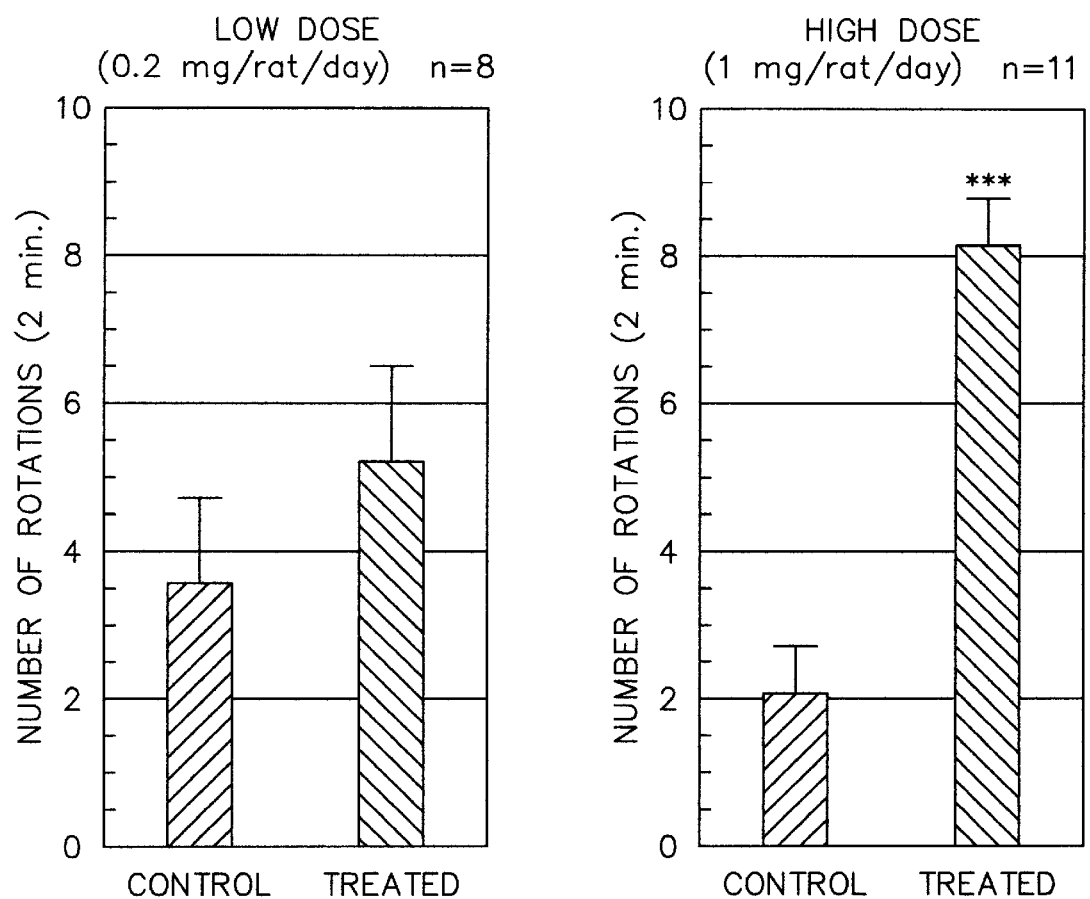
Figure 5:
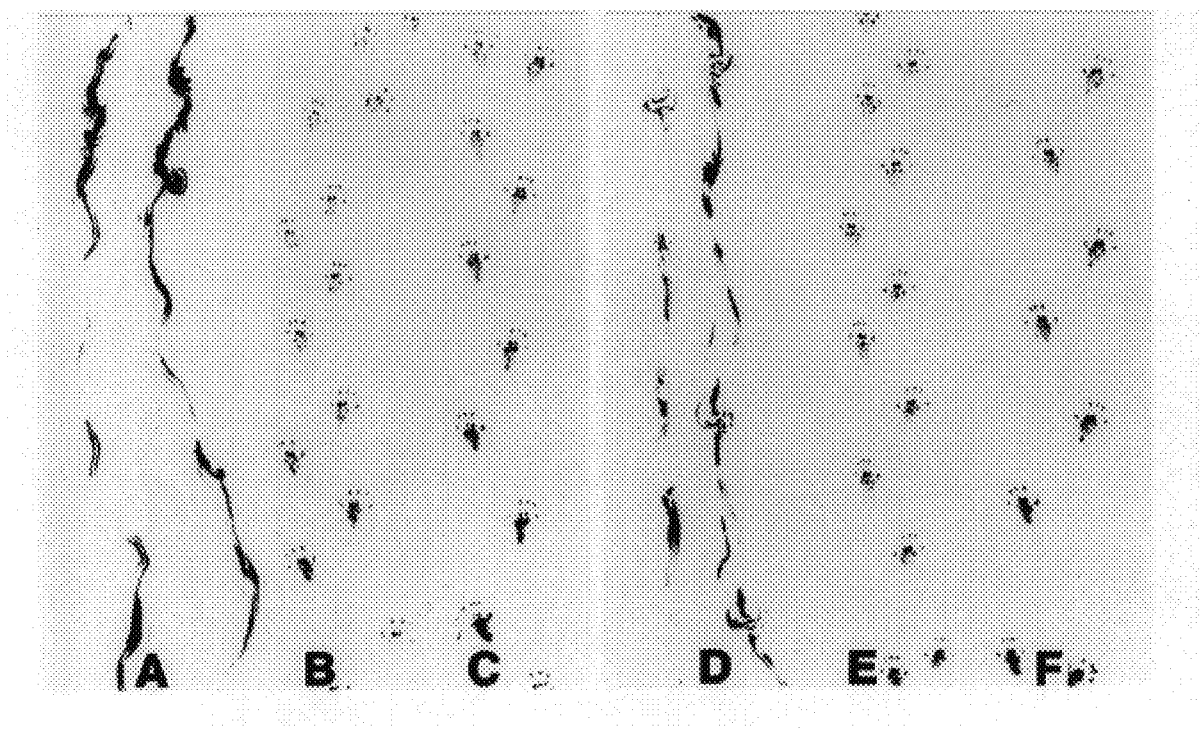
Figure 6:
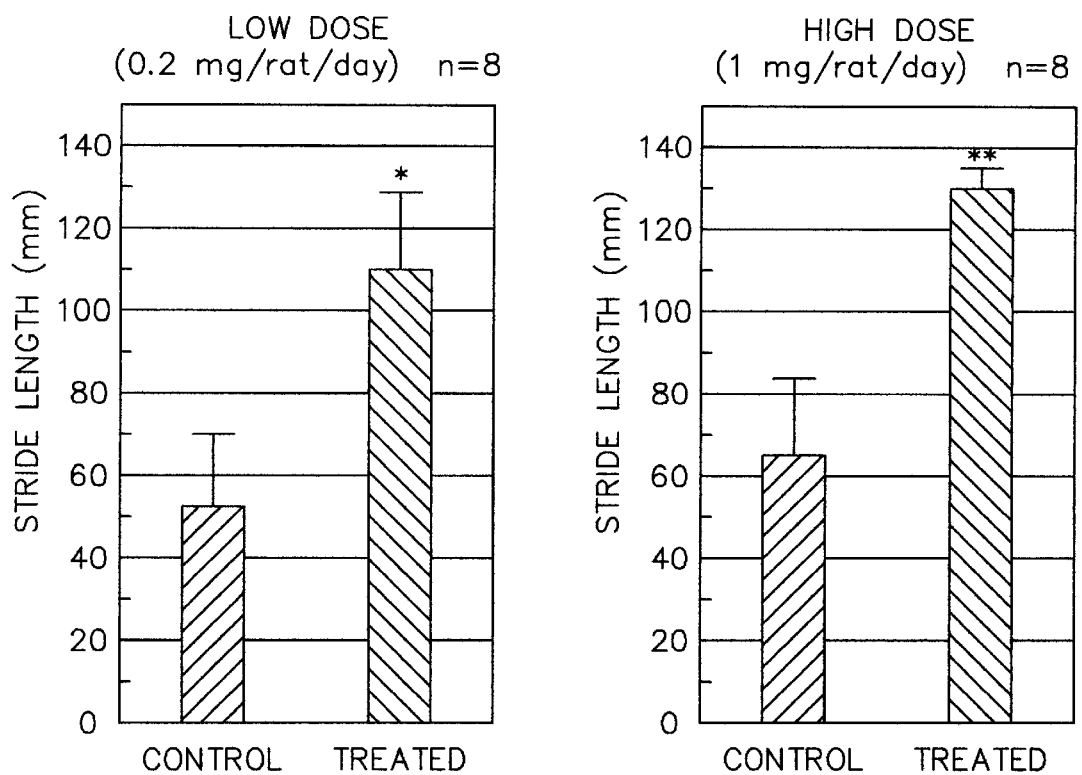
Figure 10:
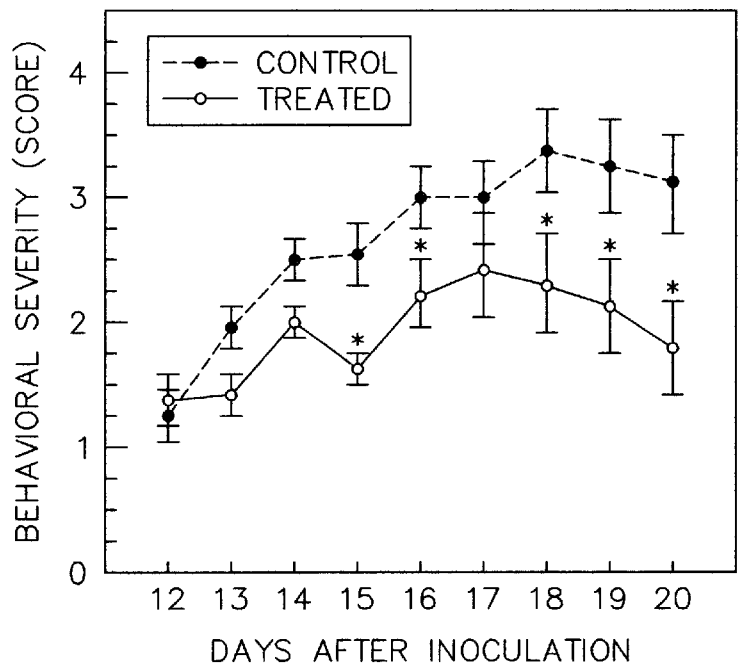
Figure 10:
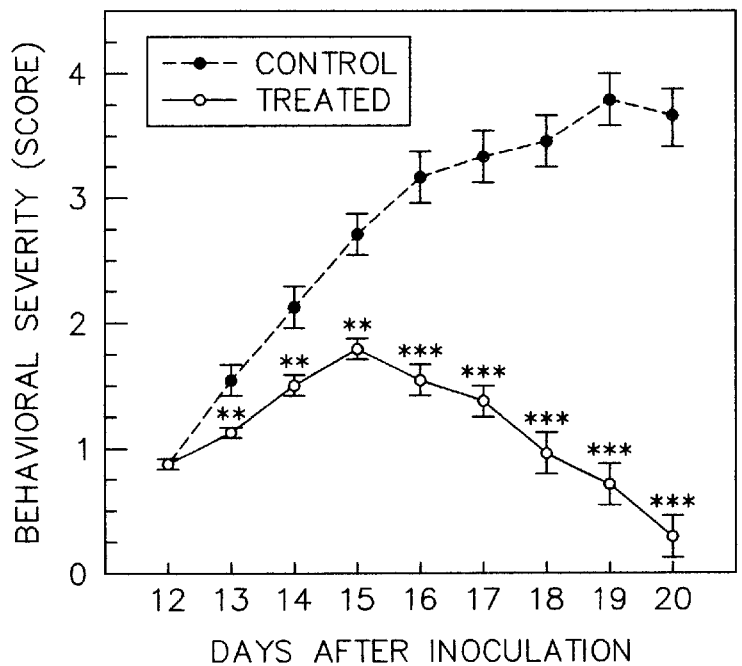

Beginning on day 12, rats with EAE were trained to walk continuously for several minutes on an exercise wheel (diameter 24 cm). On day 20, the number of wheel rotations made during 2 min of walking was recorded (FIG. 4). Placebo-treated rats were weaker, walked more slowly and produced fewer rotations than rats treated with IGF-I (FIG. 4). Mean rotations were fewer for placebo-treated rats in the second trial, a reflection of the rats' higher clinical deficit scores and variations seen in different EAE experiments (FIG. 10). Still, treadmill performance was significantly better in rats treated with the higher dose (P<0.0001) (FIG. 4). After training, rats were able to walk along a straight path, 50–60 cm long and about 20 cm wide. After 8 days of placebo or IGF-I treatment, their hind feet were inked and their footprints were recorded on white poster paper (FIG. 5). Very severe weakness associated with dragging of hind limbs was easily identified in placebo-treated rats (FIG. 5A and D). In other placebo-treated rats, steps were short when weakness was moderate (FIG. 5B and E) and were longer in IGF-I treated rats with less severe weakness (FIG. 5C and F). These footprint records also permitted measurement of stride lengths and more quantitative comparison of IGF-I and placebo-treated groups (FIG. 6). Differences in the stride lengths of placebo and IGF-I-treated rats were significant (P<0.05–0.01) and also dose-dependent (FIG. 6).

Blood-brain barrier changes

Figure 7:
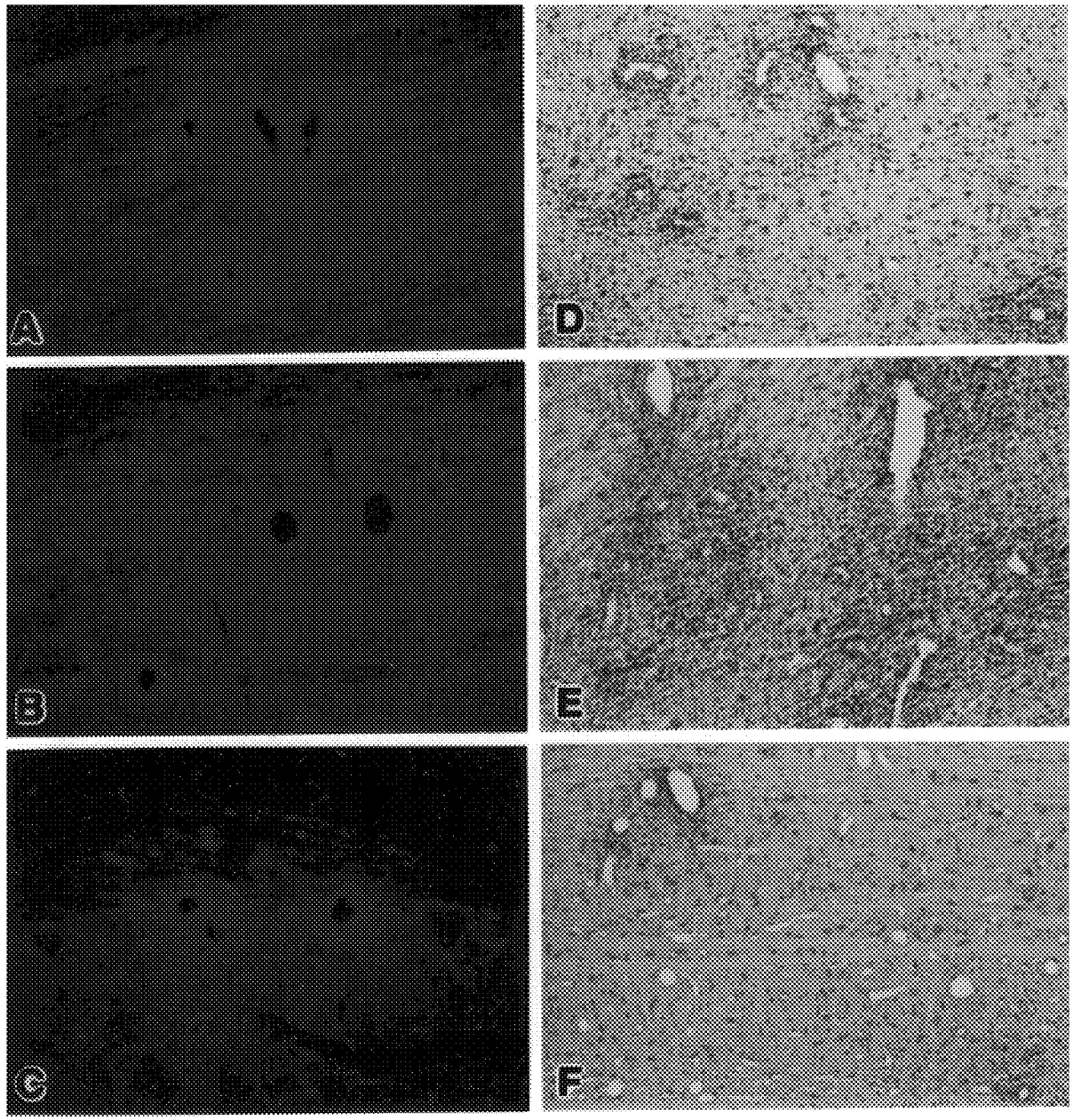

On day 12 of EAE, just before treatment began, spinal cord sections contained large areas of perivascular fluorescence in both gray and white matter. These areas corresponded to widespread leakage of intravascular Evans blue-BSA through permeable vessels into spinal cord parenchyma (FIG. 7A). After 4 days of placebo treatment, areas of fluorescence were similar in size or slightly larger (FIG. 7B). After 4 days (FIG. 7C) and 8 days (not shown) of IGF-I treatment with 3.0 mg kg$^{-1}$ day$^{-1}$, there were fewer areas of Evans blue-BSA fluorescence and they were much smaller. Measurements of fluorescence made in comparable areas under the same illumination conditions confirmed that permeability was significantly less in IGF-I treated rats at both 16 days and 20 days (not shown).

Lesion reduction

Figure 8:
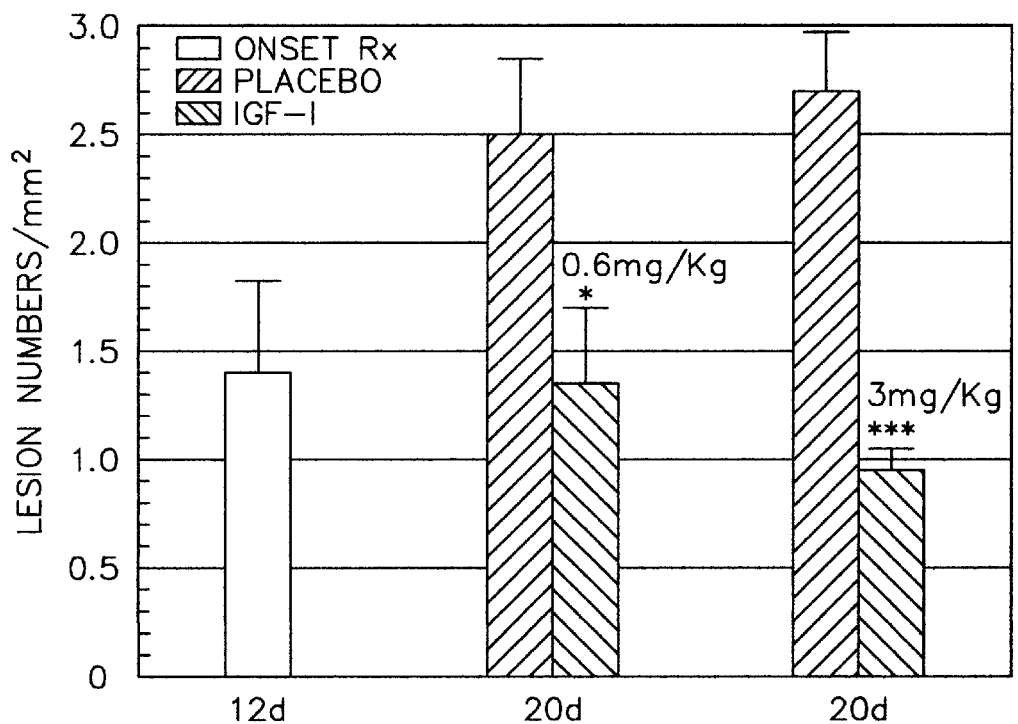
Figure 9:
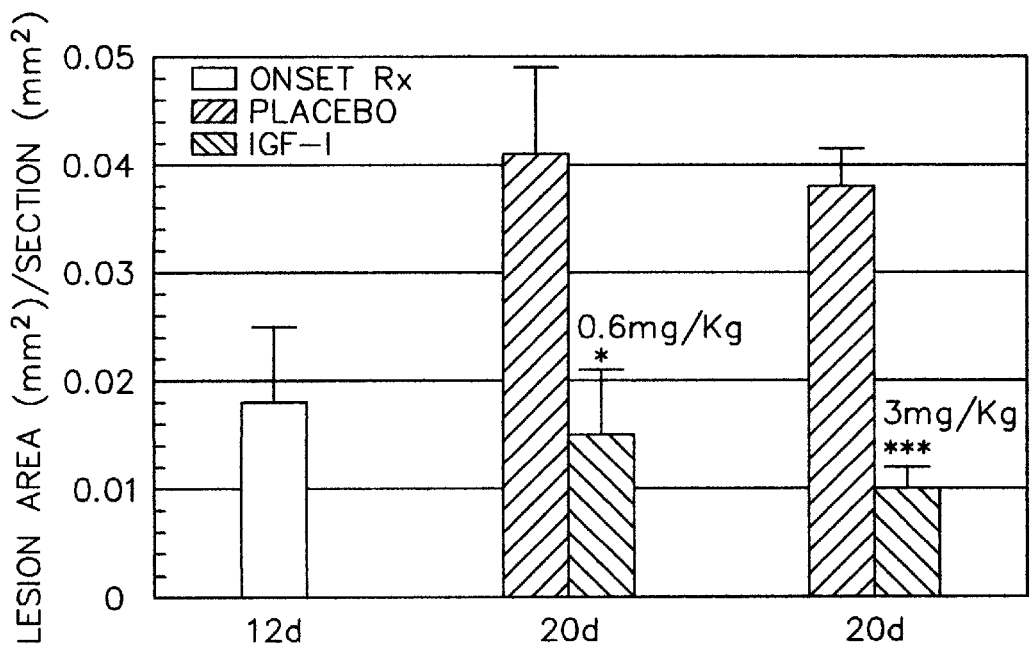

Before treatment began on day 12, there were numerous perivascular infiltrates of lymphocytes and mononuclear cells in both white and gray matter (FIG. 7D). In sections from placebo-treated rats, the lesions were much larger and more numerous at 20 days (FIG. 7E). However, lesions were fewer in number and much smaller in sections from rats which had received 3.0 mg kg$^{-1}$ of IGF-I for 8 days (FIG. 7F). To assess lesions quantitatively, they were counted and their areas were measured in sections from rats on day 12 (before treatment) and on day 20 after 8 days of placebo or IGF-I (0.6 mg kg$^{-1}$ day$^{-1}$ or 3.0 mg kg$^{-1}$ day$^{-1}$) treatment. In placebo-treated rats, lesion numbers increased by 78–96% from day 12 to day 20. In marked contrast, after 8 days of IGF-I treatment, there were 2–31% fewer lesions than at 12 days when treatment began (FIG. 8). The pattern of changes in lesion areas was similar, namely a 114–130% increase from day 12 to day 20 in placebo-treated rats. Areas in IGF-I-treated rats were 16–39% less than those observed when treatment began and about 150% less than those measured in rats treated with placebo injections for the same period (FIG. 9). The results were completely unexpected, i.e., the treatment with IGF-I led to shrinkage and/or loss of lesions.

Behavioral tests and body weights

Pairs of rats with EAE which were selected on day 12 for all three treatment trials had equally severe tail and mild hind limb weakness. Their clinical severity scores were 1–1.5 just before the first i.v. injection (FIG. 10). From days 12–20, placebo treated rats became weaker with peak mean deficit scores of 3.5–3.8 on days 18–19. They still were severely impaired (3.0–3.5) on day 20.

In contrast, maximum clinical deficit levels in rats treated with IGF-I were significantly lower (P<0.05–0.0001) and occurred earlier (FIG. 10). These treatment effects were also dose-dependent. For rats treated with 0.6 mg kg$^{-1}$ day$^{-1}$, the peak deficit was 2.4 on day 17 with improvement to 1.8 by day 20. A higher dose (3.0 mg kg$^{-1}$ day$^{-1}$) prevented severe deficits. Peak levels were only 1.8 and occurred 3 days after starting treatment. The rats recovered rapidly during the remaining 5 days of treatment and they were almost normal neurologically on day 20 (FIG. 10).

Figure 11:
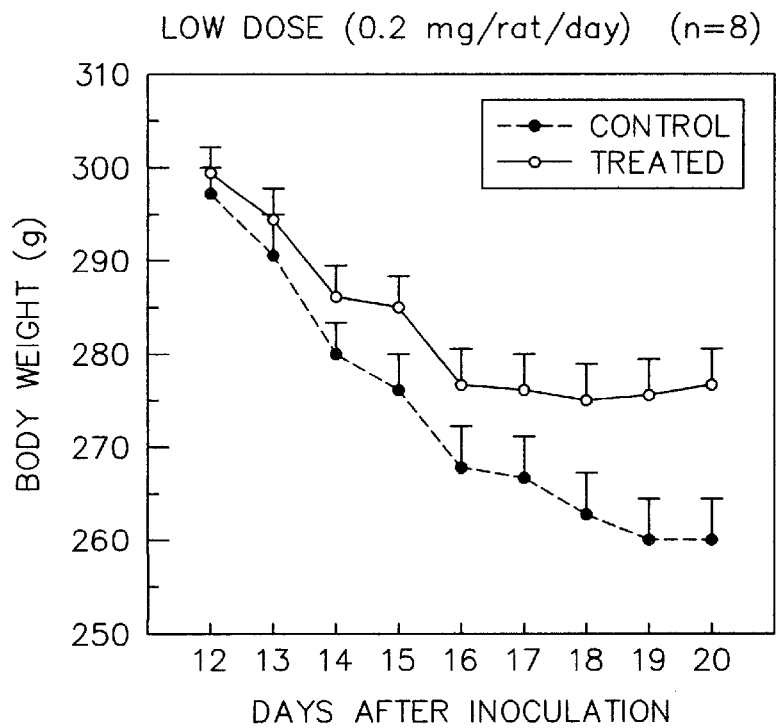
Figure 11:
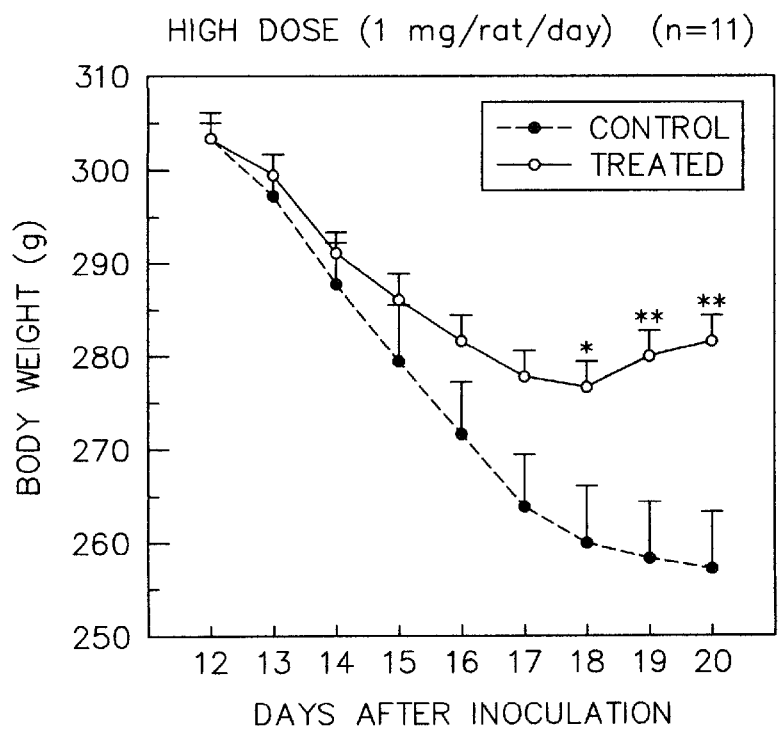

Rats receiving placebo treatment lost weight daily from day 12 to day 20 of EAE (FIG. 11). However, those treated with IGF-I lost substantially less weight and began gaining on day 17–18. As with clinical scores, weight loss differences were dose dependent and were significant by day 18–20 (P<0.05–0.01) (FIG. 11).

EXAMPLE 2

Subcutaneously administered IGF-I reduces lesion severity and behavioral deficits Example 2 illustrates the efficacy of subcutaneous administration of IGF-I on treatment of lesions in acute demyelinating EAE.

Induction of EAE, Clinical Evaluation, IGF-I Treatment

EAE was induced in 30 anesthetized adult male Lewis rats (300±20 g) with an emulsion containing guinea pig spinal cord and complete Freunds adjuvant as described generally in Example 1. Twelve days after immunization, when mild, definite weakness was first detected, 16 rats with identical clinical deficits were identified. Eight were given 100 μg rhIGF-I every 12 hr for 8 days, either subcutaneously (3 rats) or intravenously (5 rats) as previously described in Example 1. The remaining 8 rats received subcutaneous or intravenous placebo injections of 0.85% saline on the same schedule. The volume of each IGF-I and placebo injection was 0.4 ml.

On day 10, the rats were asymptomatic and were given code numbers. They were weighed and tested twice daily by an observer unaware of the treatment. On day 12, clinical deficits appeared and were scored from 1–5. Gait was tested by counting exercise wheel rotations per 2 min and by measuring stride length as described in Example 1. Body weights, clinical scores, wheel rotations and stride lengths were expressed as means±S.E. Student t-tests with two tailed P values were used to compare rats given IGF-I (s.c.), IGF-I (i.v.), or placebo by the same route; differences were considered significant when P<0.05. After 8 days of treatment, the rats were anesthetized and sacrificed. All procedures were included in an approved Animal Use Protocol and met National Institutes of Health Guidelines for the Use of Animals in Research.

Immunocytochemistry and In Situ Hybridization

After spinal cord removal, upper lumbar and thoracic segments were fixed in 4% paraformaldehyde, embedded in paraffin and coded for blind evaluation. Longitudinal sections were immunostained with polyclonal antimyelin basic protein (MBP) according to previously described methods (Yao et al, *J. Neurosci. Res.* 40:647–659 (1995); Yao et al, *Proc. Natl. Acad. Sci. USA* 92:6190–6194 (1995)). Bioquant OS/2 software was used to determine numbers and areas of demyelinating lesions in four non-overlapping sections from each rat. Means±S.E. were calculated and when P<0.05, differences between IGF-I and placebo-treated rats were considered significant.

Lower lumbar and thoracic segments were frozen and used for in situ hybridization. Procedures, synthetic oligonucleotide probes specific for MBP, PLP (proteolipid protein), and CNP (cyclic nucleotide 3'-phosphodiesterase), and the techniques for analyzing x-ray autoradiograms have been described (Yao et al, *J. Neurosci. Res.* 40:647–659 (1995); Yao et al, *Proc. Natl. Acad. Sci. USA* 92:6190–6194 (1995)). Mean densities (average grey levels of pixels in a given area) were measured in arbitrary units in comparable areas of 8 non-overlapping sections from each rat. Means±S.E. in IGF-I- and placebo-treated rats were expressed as percentages of grain densities determined in similar section areas from normal rats.

Clinical Tests

Figure 12:
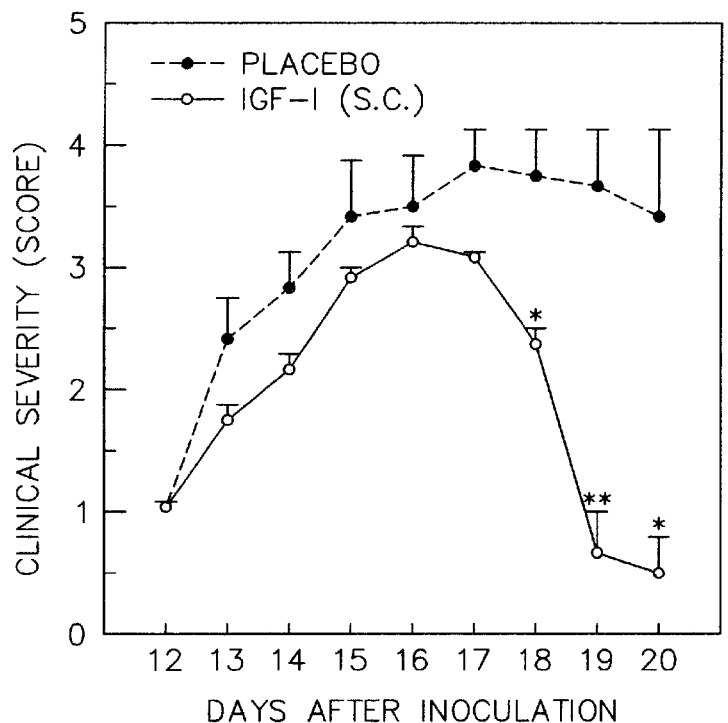
Figure 12:
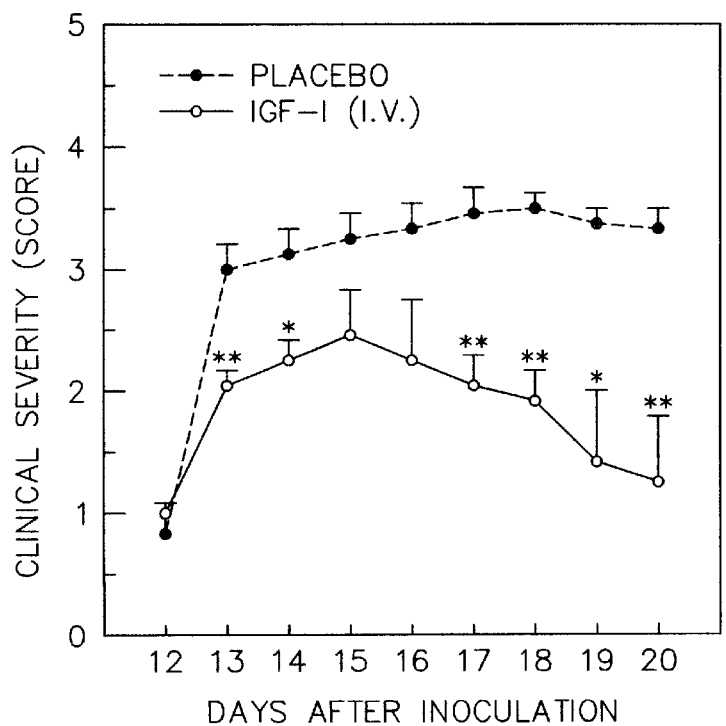
Figure 13:
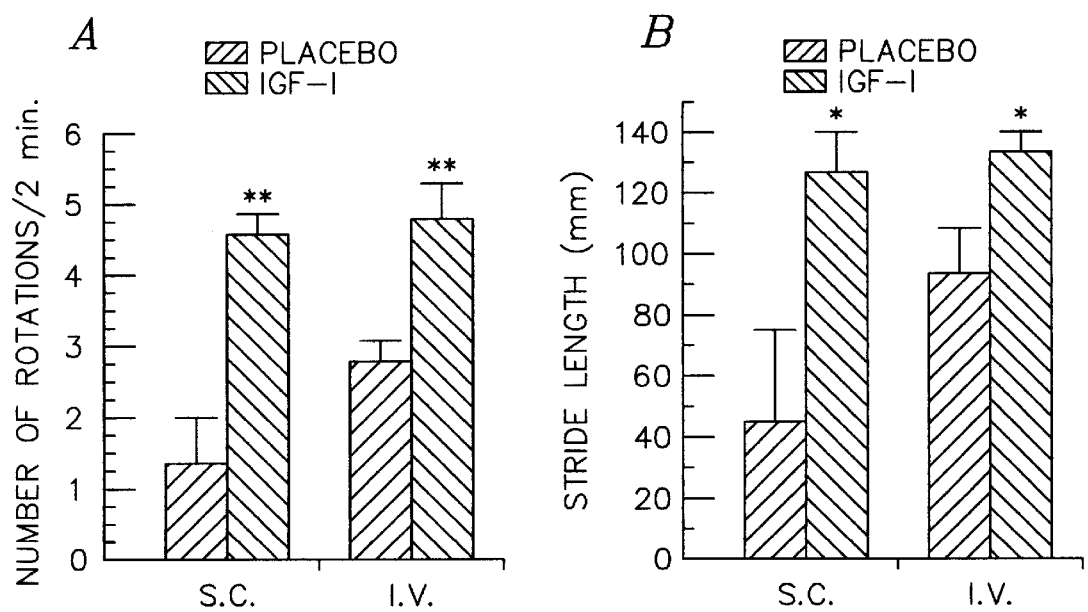

Pairs of rats selected on day 12 for comparisons of IGF-I and placebo treatment had equally severe tail and mild hind limb weakness with average clinical deficit scores of about 1 before the first i.v. or s.c. injection (FIG. 12). From day 12 to day 17 or 18, placebo-treated rats became weaker with mean peak deficit scores of 3.5–3.8 and only slight recovery to about 3.2 by day 20. In contrast, s.c. IGF-I was associated with a slightly earlier and lower peak deficit (day 16, deficit 3.2) before rapid and dramatic clinical recovery to almost normal clinical scores by day 20 (FIG. 12A). When IGF-I was given i.v., peak deficits were lower (about 2.5) and occurred earlier (day 15). Recovery was more gradual and deficits of about 1.2 were reached by day 20 (FIG. 12B). Counts of exercise wheel rotations (FIG. 13A) and measurements of stride lengths on day 20 (FIG. 13B) also showed that both groups of IGF-I-treated rats had significantly less weakness and more uniform performance levels than those given placebo injections. Finally, compared to placebo treatment, both s.c. and i.v. IGF-I decreased EAE-associated weight loss significantly (data not shown).

Demyelination and mRNA Levels of Myelin Proteins

Figure 14:
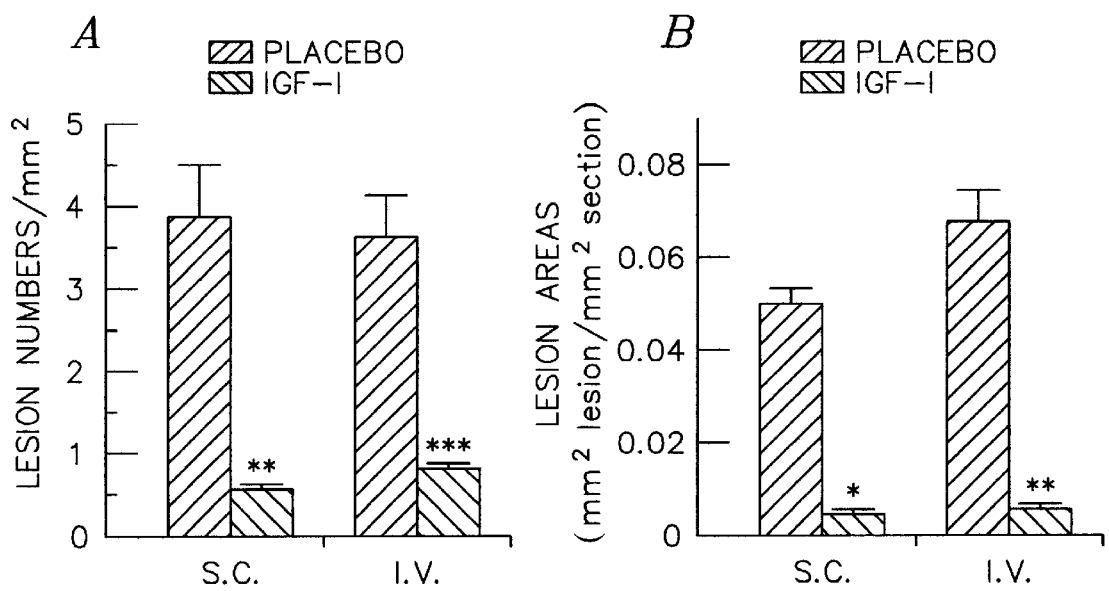

In longitudinal spinal cord sections of rats treated with placebo injections for 8 days, the large perivascular inflammatory lesions associated with demyelination resembled those described and illustrated previously (Liu et al, *Mol. Cell. Neurosci.* 5:418–430 (1994); Liu et al, *Mult. Scler.* 1:2–9 (1995)). Their numbers and areas were determined and compared with those found in similar spinal cord sections from rats treated with either subcutaneous or intravenous IGF-I (FIGS. 14A, 14B). In sections from both groups of IGF-I treated rats, the mean numbers of lesions were reduced by 77–85% and the areas were 88–92% less than they were in placebo-treated rats. Both of these differences in numbers and areas were statistically significant. However, when lesion numbers and areas were compared in sections from rats given either s.c. or i.v. IGF-I, no significant statistically differences were found, indicating that both injection routes provided similar reductions in demyelinating lesion severity.

Figure 15A:
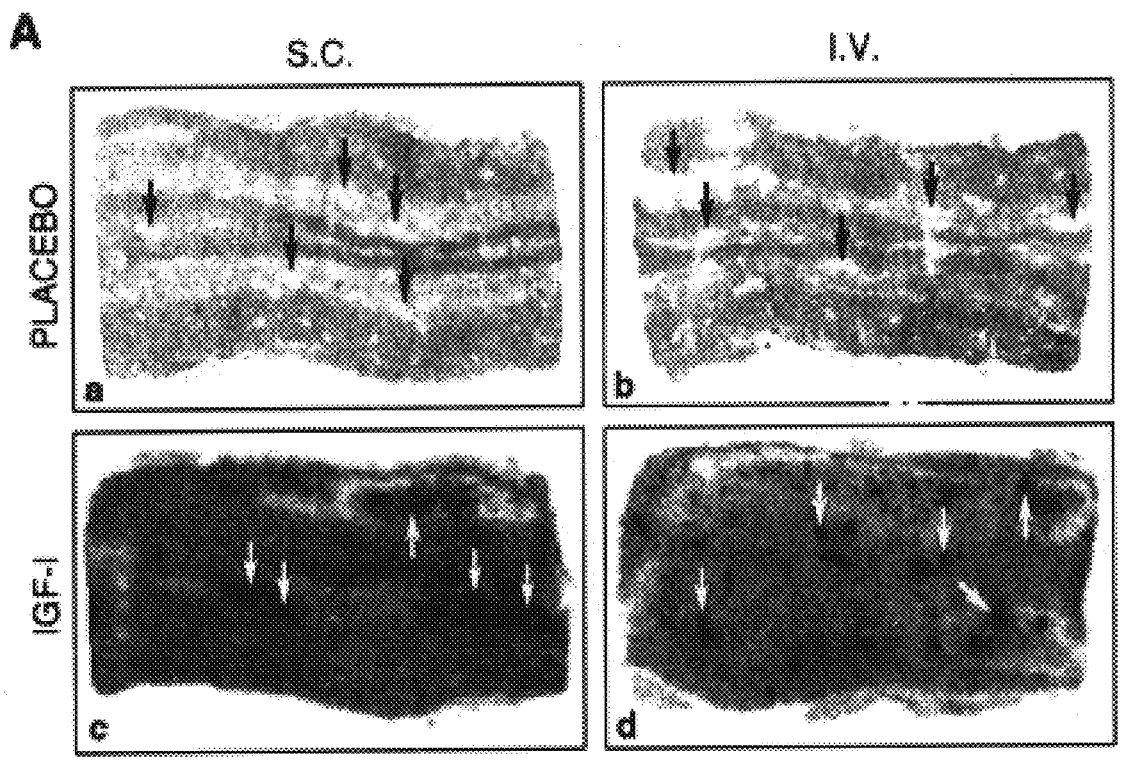
Figure 15B:
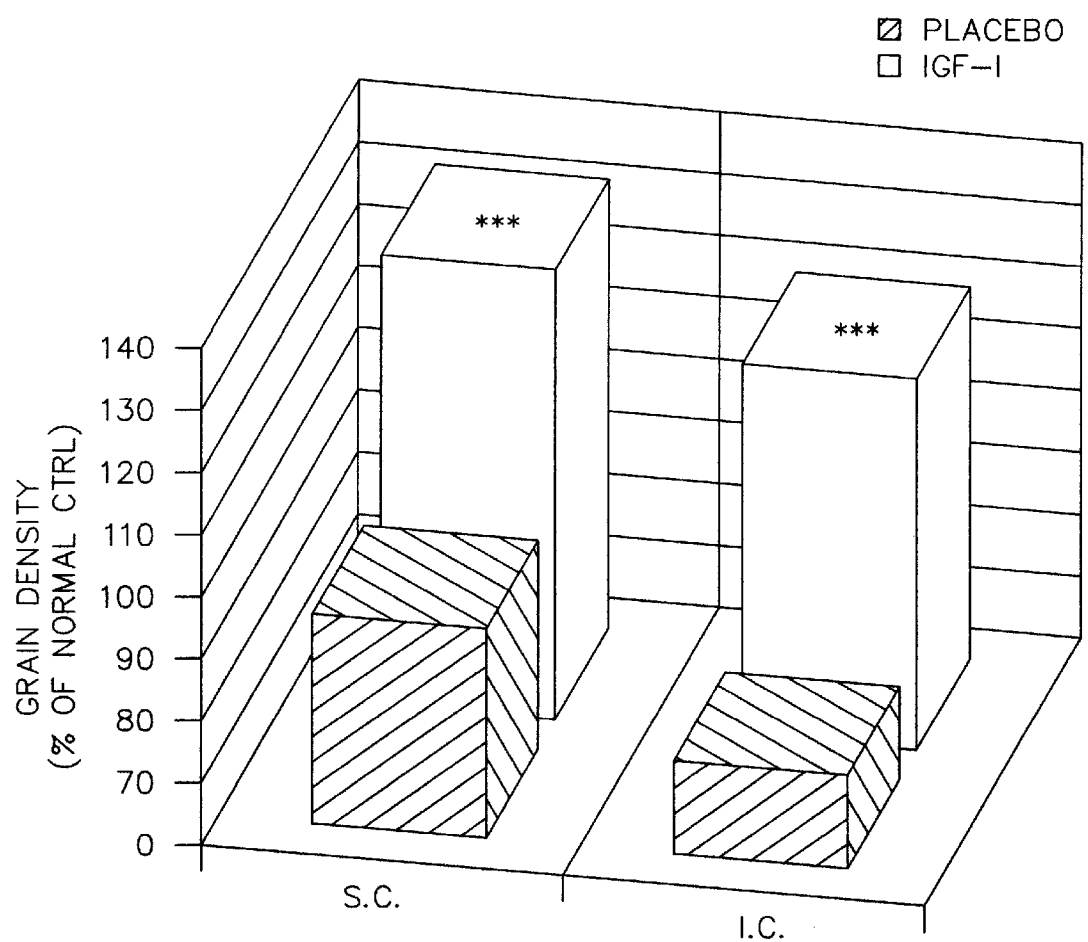

Computer-assisted analysis of relative grain densities on x-ray film autoradiograms provided semiquantitative comparisons of relative mRNA levels for MBP (FIGS. 15A, 15B). In autoradiograms of sections from rats treated for 8 days with placebo injections, relative MBP mRNA levels were lower in areas with inflammation and demyelination than they were in surrounding histologically normal areas (FIG. 15A, a, b). In autoradiograms of sections from rats treated with either s.c. (FIG. 15A, c) or i.v. IGF-I (FIG. 15A, d), relative MBP mRNA levels in lesion areas were much higher than those in lesions of placebo-treated rats (P<0.0001) (FIG. 15B). Comparable, equally significant increases were observed in relative mRNA levels for PLP and CNP in autoradiograms of sections from both groups of IGF-I-treated rats (data not shown).

EXAMPLE 3

IGF-I reduces immune cell responses in adoptive transfer EAE

Example 3 sets forth three different experiments which examine IGF-I effects on immune-mediated inflammation in an EAE model which primarily evidences perivascular lesions without significant demyelination. I.e., this is unlike the models of Example 1 and Example 2 which include demyelination. So in Example 3, EAE was induced in Lewis rats by passive transfer of myelin basic protein (MBP)-reactive T lymphocytes. The results indicate that IGF-I treatment significantly reduced clinical deficits and lesion severity. Immune cell responses also were changed. In all of the experiments, the procedures were included in approved Animal Use Protocols and met Max Planck Institute and National Institutes of Health Guidelines for the Use of Animals in Research.

T Cell Lines

Figure 16:
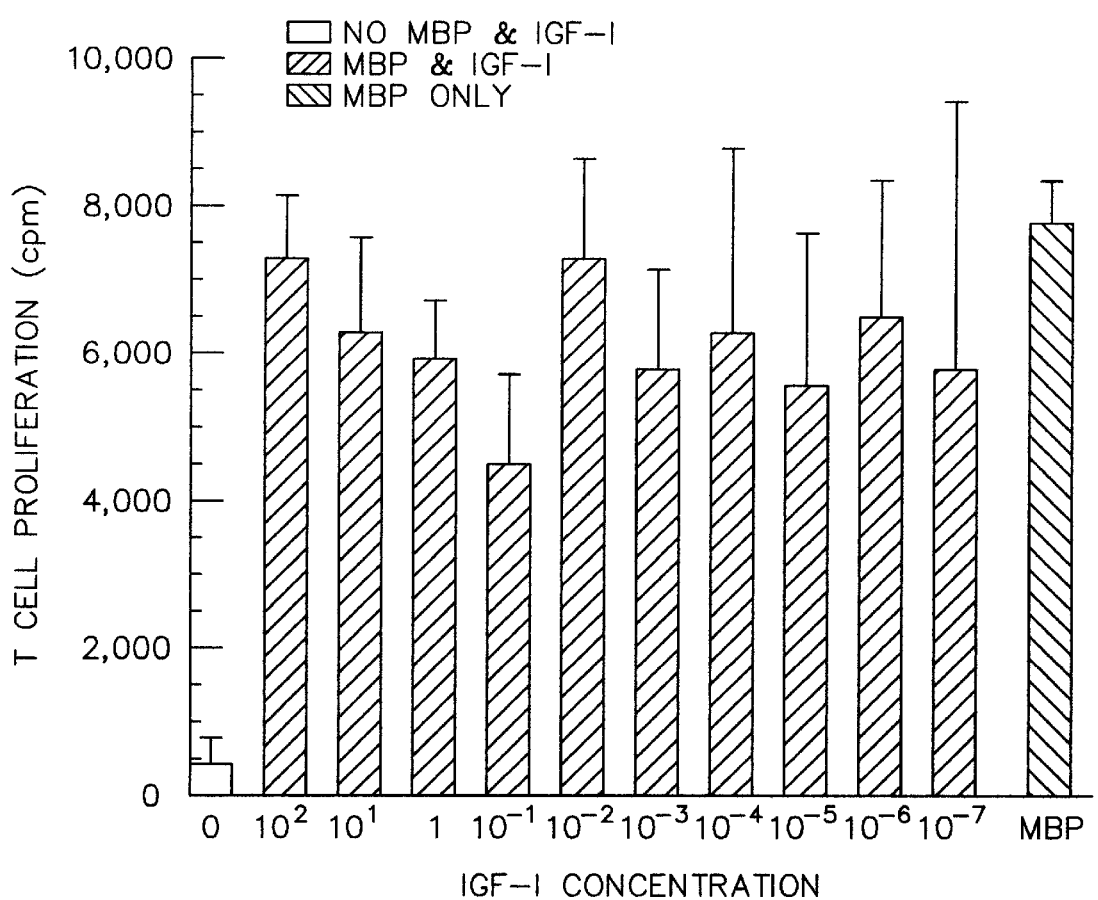

T cell lines responding to purified protein derivative of tuberculin (PPD) or MBP were established by the primary limiting dilution method ("split well culture") of Pette and collaborators (1990). Briefly, adult Lewis rats were immunized with an emulsion containing PPD or guinea pig MBP. T cells were isolated from draining popliteal lymph nodes and maintained in culture by alternating rounds of PPD or MBP activation and cytokine-driven proliferation. Antigen-specific T cell lines were selected by repeated cycles of propagation in T cell growth factor-containing medium followed by restimulation using irradiated syngeneic thymocytes as antigen-presenting cells in the presence of PPD or guinea pig MBP. T cell proliferation was assessed by the addition of [$^3$H] thymidine (1 $\mu$Ci/well) for the last 16 hr of a 72 h culture. After harvesting the cells onto glass-fiber filters, a Packard direct beta counter Matrix™ 96 was used to determine the uptake of [$^3$H] thymidine. T cell proliferation was determined after 16 hr incubation in medium alone and medium containing MBP. The proliferation observed when $10^2$–$10^{-7}$ $\mu$g/ml IGF-I was added to the MBP-containing medium was not significantly different from that observed with MBP alone (FIG. 16).

Induction of EAE and IGF-I Treatment
Trial No. 1:

In the first IGF-I treatment trial, 34 adult (250–300 g) Lewis rats received $5\times10^5$ MBP-specific T cells intravenously. The rats were weighed and examined twice daily for clinical signs of EAE. Clinical deficits were graded as follows: (1) normal except for flaccid tail; (2) weakness of tail and hind limbs, mild ataxia; (3) moderate paraparesis or severe ataxia; (4) some forelimb weakness, severe paraparesis, episodes of incontinence; (5) no hind limb movement, incontinent, impaired respiration, or moribund. On day 4, when mild but definite weakness was first detected, 10 pairs of rats with the same clinical deficit scores were identified. Ten were given 300 µg of rhIGF-I intravenously in the tail vein every 12 h for 6 days. The other 10 received i.v. placebo (0.89% NaCl) injections according to the same schedule. On day 8, after 4 d of treatment, 4 pairs of rats were euthanized with an anesthetic overdose. Their spinal cords were removed rapidly and segments were either quick frozen for cryostat sectioning or fixed in formalin and either embedded in paraffin or postfixed in osmium tetroxide before epoxy resin embedding. On day 10, after 6 d of treatment, the remaining 6 pairs of rats were euthanized; their spinal cords were processed in the same manner for longitudinal frozen and paraffin sections and for transverse toluidine-blue stained semithin sections.

Trial No. 2

The second trial included nine pairs of rats which had been given $5\times10^5$ MBP-specific T cells. However, in contrast to the first trial, treatment was started on the day after immunization, 3 d before clinical deficits appeared. The doses and injection schedules of IGF-I (300 µg i.v. q 12 hr) and placebo were the same. Pairs of rats were sacrificed after 7 d and 11 d of treatment (8 d and 12 d after immunization) and their spinal cords were processed for frozen, paraffin and epoxy resin sectioning as described above.

Trial No. 3

In the third treatment trial, 36 rats received intravenous injections of $1.5\times10^6$ activated MBP-specific T cells. On day 4, 13 pairs with the same deficits were selected; thirteen received the above dose of IGF-I i.v. q 12 h; the other 13 received placebo injections. On day 5, four rats died. Three had been treated with placebo, and one had received two injections of IGF-I. Treatment was stopped on day 6 because of rapidly progressing EAE. The other 22 rats died during the next 3 days.

Methods Protocol

Histology, Immunocytochemistry and In Situ Hybridization

Two non-overlapping longitudinal paraffin-embedded sections were stained with hematoxylin and eosin (H&E) and examined with the slide labels covered. Lesions in each section were identified and counted. The section area as well as areas occupied by lesions were measured using Bioquant image analysis software. Means and standard errors of lesion numbers and lesion areas per $mm^2$ of section area were calculated for IGF-I- and placebo-treated groups and compared using Student t-tests. Differences were considered significant if P<0.05. Semithin sections stained with toluidine blue were used to detect demyelination and compare lesions with those seen in a different EAE model, i.e., the EAE model of Examples 1 and 2 where lesions and demyelination were induced. Demyelination was also assessed by immunostaining other paraffin sections with polyclonal anti-MBP (1:100, Dako, Carpenteria, Calif.) according to the ABC method as previously described (Hsu et al, 1981; Liu et al, 1994).

Immune cells were identified in serial longitudinal cryostat sections which were fixed for 5 min in 3.7% paraformaldehyde, dehydrated in acetone, and immunostained according to the ABC method (Hsu et al, 1981). Nonspecific staining was blocked by incubation in 10% normal horse serum (Vector Laboratories, Burlingame, Calif.) for 30 min. Incubations in primary antibodies were overnight at 4° C. in one of the following: monoclonal anti-ED-1 (1:1000, Serotec, Oxford, UK), anti-CD4 (1:100, Serotec), anti-CD8 (1:100, Serotec), anti-CD43 (1:500, Serotec), and anti-α/β TCR (1:100, Serotec). Incubations in biotinylated secondary antibodies (ABC Elite kit, Vector Laboratories) were 1 hr at room temperature and the detection substrate was 3,3' diaminobenzidine.

Lower thoracic and lumbar spinal cord segments were frozen and used for in situ hybridization. Our procedure, the synthetic oligonucleotide probe specific for MBP and our techniques for analyzing x-ray autoradiograms have been described (Yao et al, 1995a; Yao et al, 1995b). Mean densities (average grey levels of pixels in a given area) were measured in arbitrary units in comparable areas of non-overlapping sections from each rat. Means±S.E. in IGF-I- and placebo-treated rats were expressed as percentages of grain densities determined in similar section areas from normal rats.

Results a. Clinical tests and body weights

Figure 17:
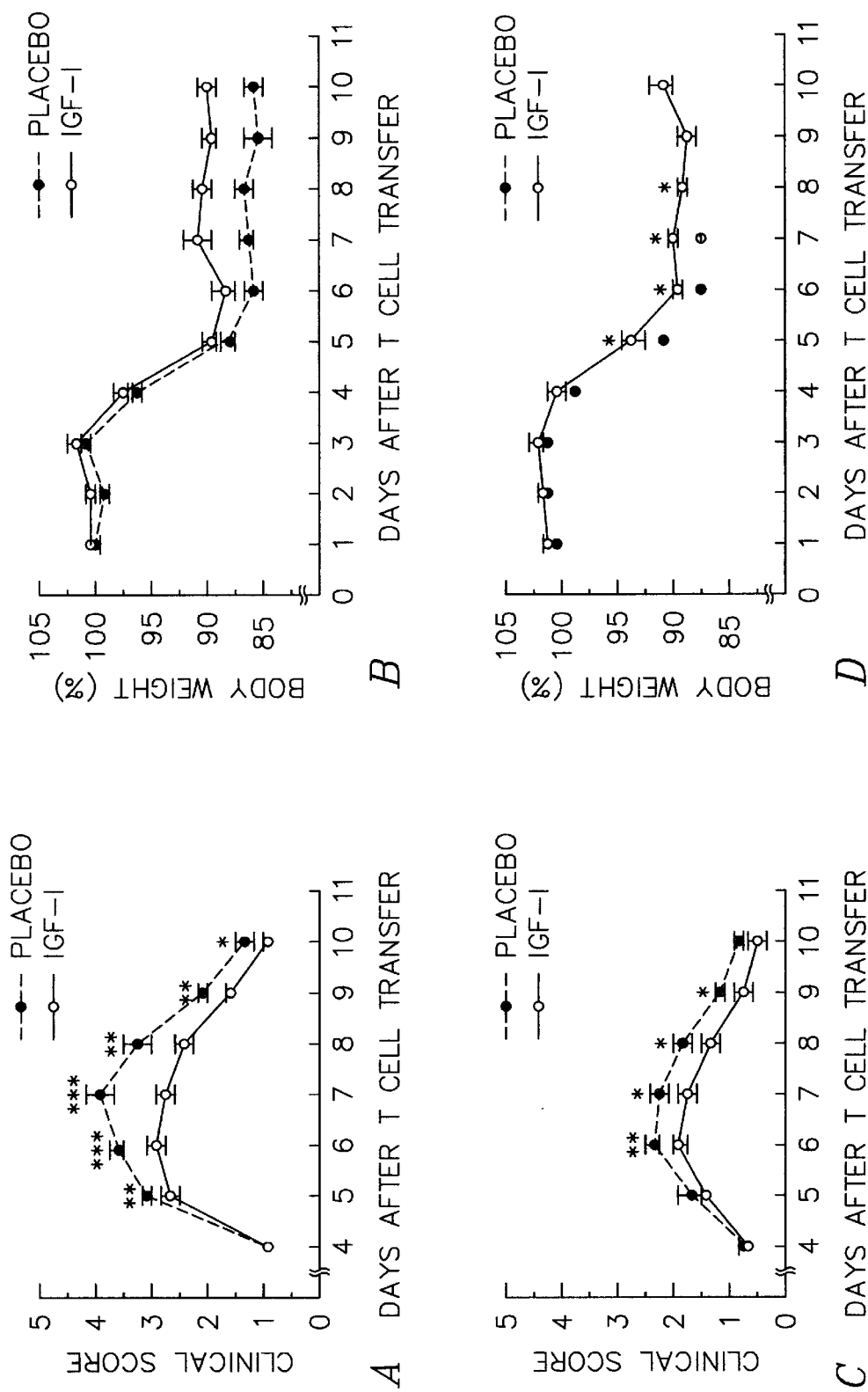

The first trial included 10 IGF-I- and 10 placebo-treated rats; treatment began on day 4 when grade 1 deficits and weight loss were first noted (FIG. 17A, 17B). By day 5, the IGF-I- treated rats had less severe deficits and had lost less weight. Their deficits and weight loss reached maximum levels on day 6, were significantly less than those observed in placebo-treated rats, and were followed by earlier, more rapid recovery (FIGS. 17A, 17B).

In the second trial, treatment of 9 pairs of rats began the day after immunization. Three days later, slight weakness and weight loss were first noted. Although progression occurred, the maximum clinical deficit levels and weight loss percentages were less than in the second trial. Even so, rats receiving IGF-I had significantly lower clinical scores on days 6–9; they also lost less weight (FIGS. 17C, 17D).

Comparison of IGF-I and placebo treatment effects in the third trial (26 rats) was not possible because of rapidly progressive EAE. All 26 rats had succumbed 8 days after cell transfer and only 4 days after symptoms first appeared.

b. Lesions, immune cells, blood-brain barrier, MBP mRNA

1. Trial No. 1

Figure 18:
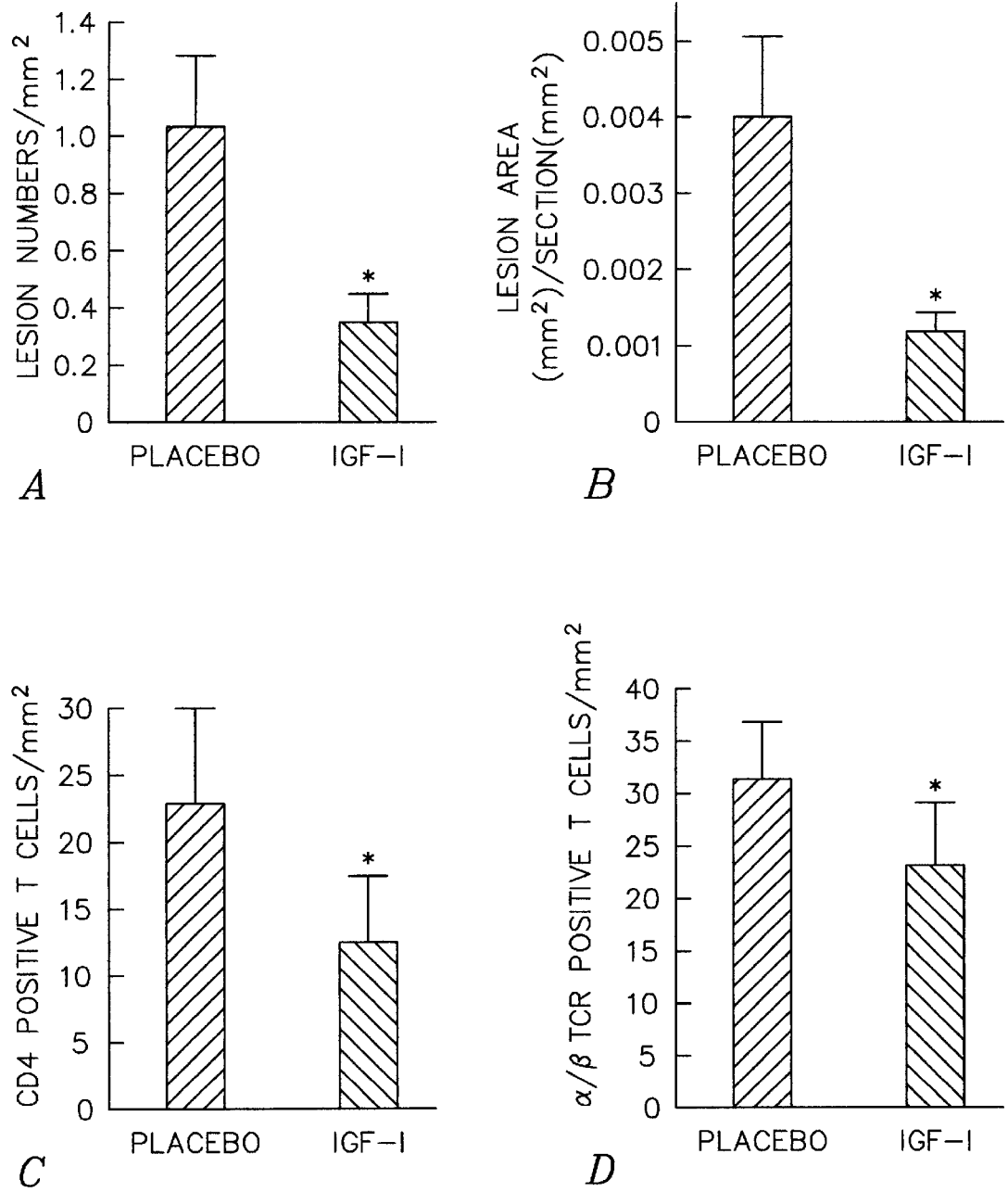

In the first trial, treatment began 4 days after immunization, when symptoms and weight loss were first observed. After 4 and 6 days of treatment, H&E-stained spinal cord sections of rats contained perivascular inflammatory lesions which resembled those described previously (Lassmann et al, 1988). When studied morphometrically, the sections from rats treated with IGF-I for 4 d contained 35% fewer lesions than those from placebo-treated rats. After 6 days of treatment, the IGF-I-induced reduction in lesion number was 60% (FIG. 18A). Lesion areas were reduced by 50% at 4 d and 70% at 6 d (FIG. 18B). No demyelination was observed in Luxol fast blue-stained sections, in those immunostained with anti-MBP, or in semithin epoxy-embedded sections stained with toluidine blue.

From Table I, it can be seen that in the placebo-treated rats, there was a 37% and 40% reduction in lesion number and size, respectively, at 6 days after treatment compared to 4 days after treatment. The lesions associated with MS naturally exhibit a "waxing and waning" characteristic. The decrease in the size and number of lesions in the placebo-treated group reflects the waning phase of this phenomenon. In spite of the waning phase, however, IGF-I treatment resulted in further reductions in both lesion size and number, as discussed above.

Figure 19:
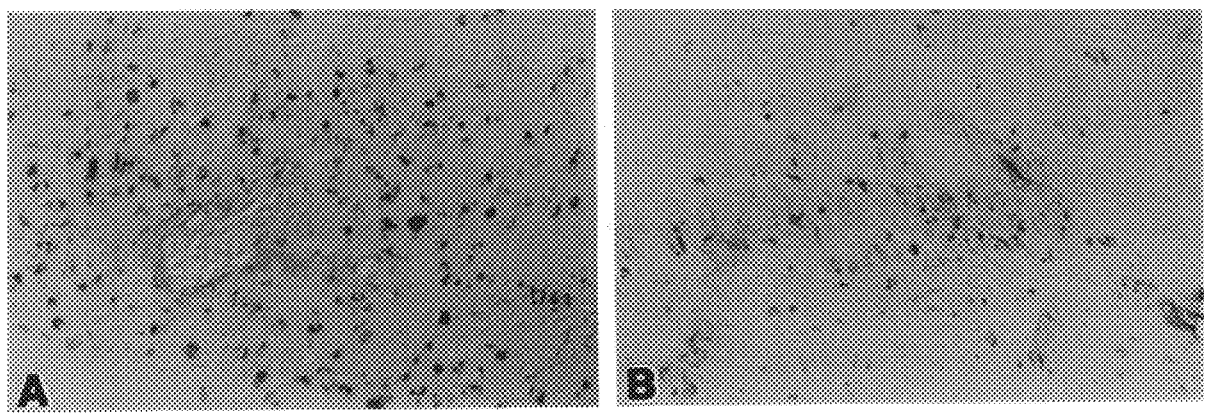
Figure 20:
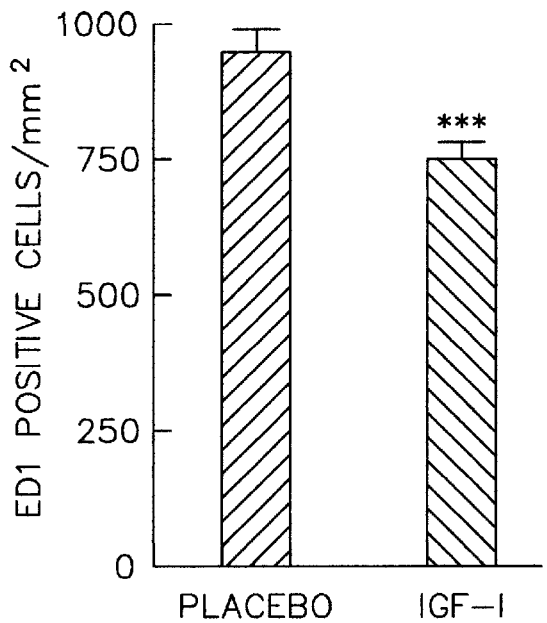

The IGF-I-induced reduction in lesion number and size was associated with a 25% reduction in numbers of CD4-positive T cells after 4 days of treatment; after 6 d, the reduction was 45% and significant (FIG. 18C). Six days of IGF-I treatment also reduced numbers of α/β TCR-positive T cells by 25% (FIG. 18D). After IGF-I treatment, the distribution of ED-1-positive macrophages differed from those observed in sections from placebo-treated rats. ED-1-positive cells were found clustered in perivascular areas and were less widely dispersed in the spinal cord white and grey matter than those observed in placebo-treated rats (FIGS. 19A, 19B). In addition, counts showed that sections from rats treated with IGF-I for 6 d contained significantly fewer (***P<0.0001) ED-1-positive cells (FIG. 20).

TABLE I

|  |  | 4 Days | 6 Days | % Change |
| --- | --- | --- | --- | --- |
| Lesion Number | Placebo | 1.6442 | 1.0391 | −37% |
|  | IGF-I | 1.0583 | 0.3584 | −66% |
| Lesion Area | Placebo | 0.0066 | 0.0040 | −40% |
|  | IGF-I | 0.0033 | 0.0012 | −64% |
| CD4 + Lymphs | Placebo | 34.229 | 22.588 | −34% |
|  | IGF-I | 25.792 | 12.454 | −52% |
| α/β TCR | Placebo | 42.348 | 31.46 | −26% |
|  | IGF-I | 31.780 | 23.51 | −26% |

Figure 21:
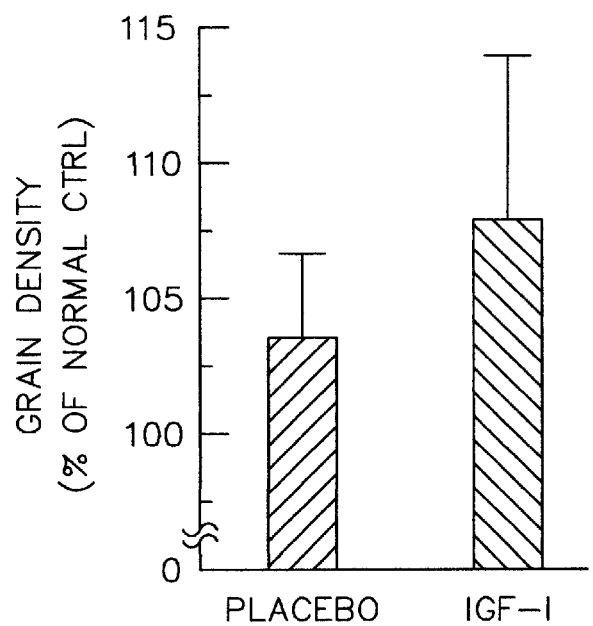
Figure 22:
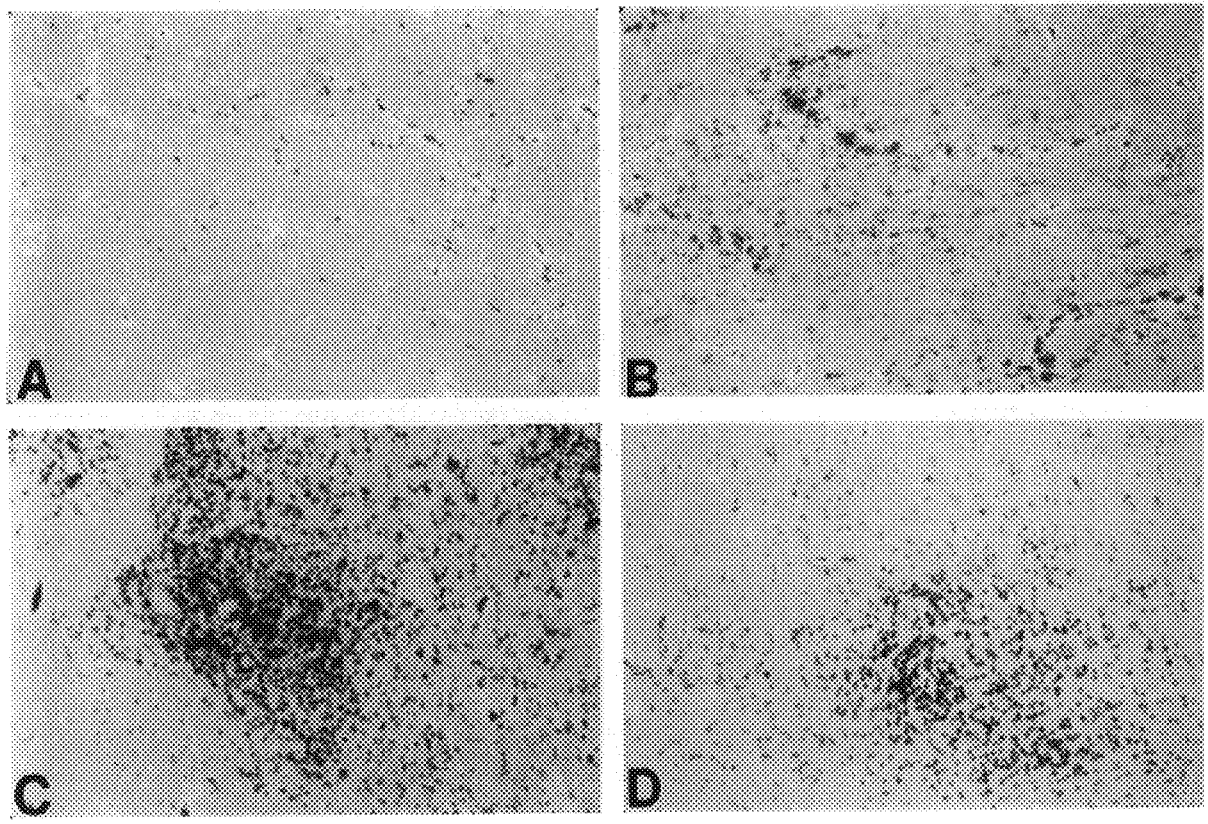
Figure 23:
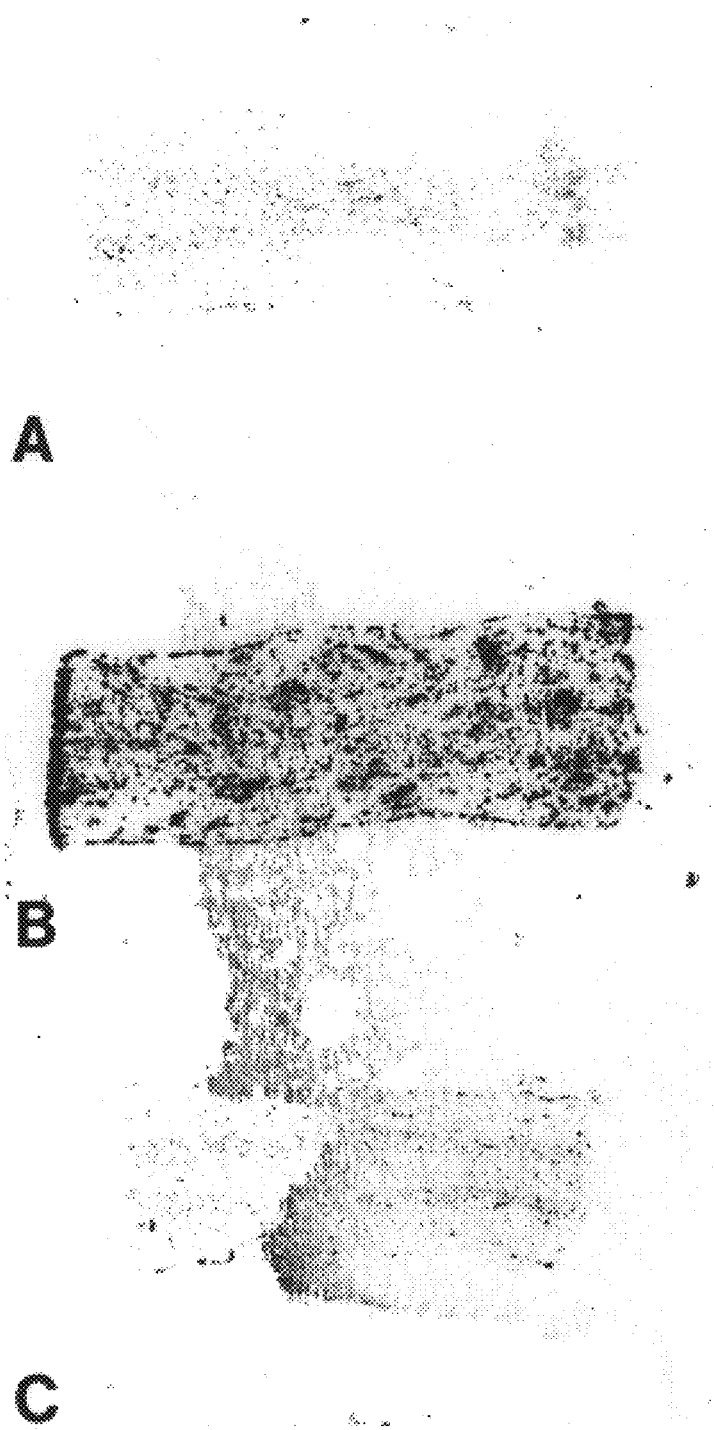
Figure 24:
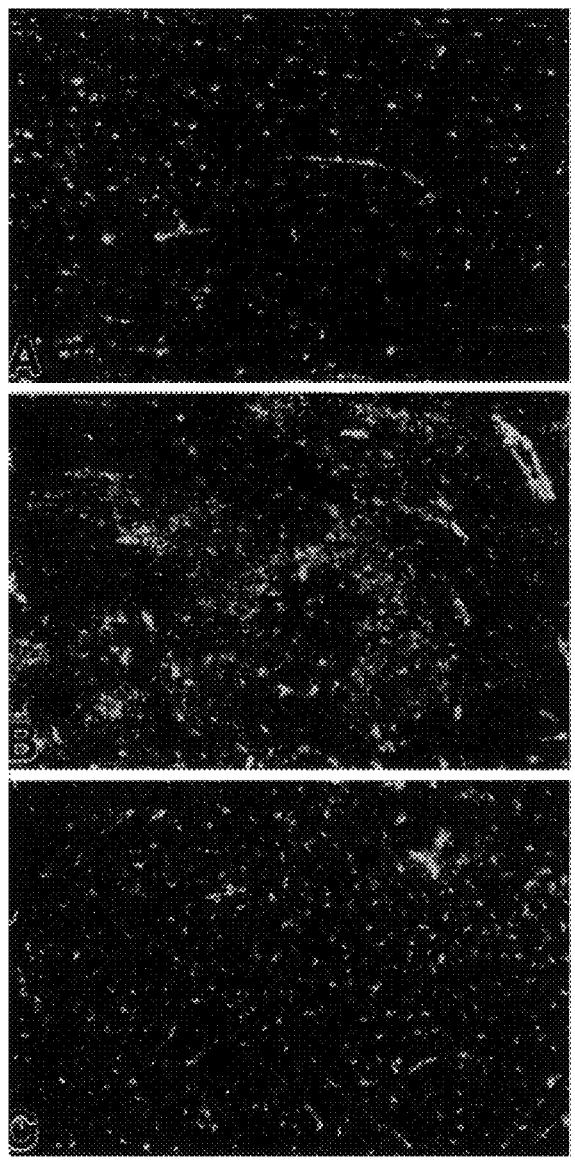
Figure 24:
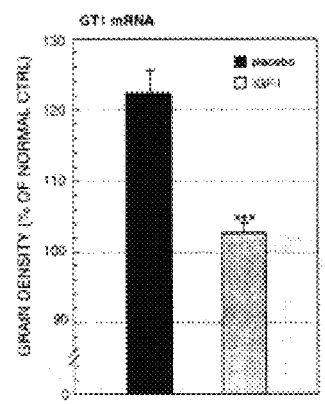
Figure 25:
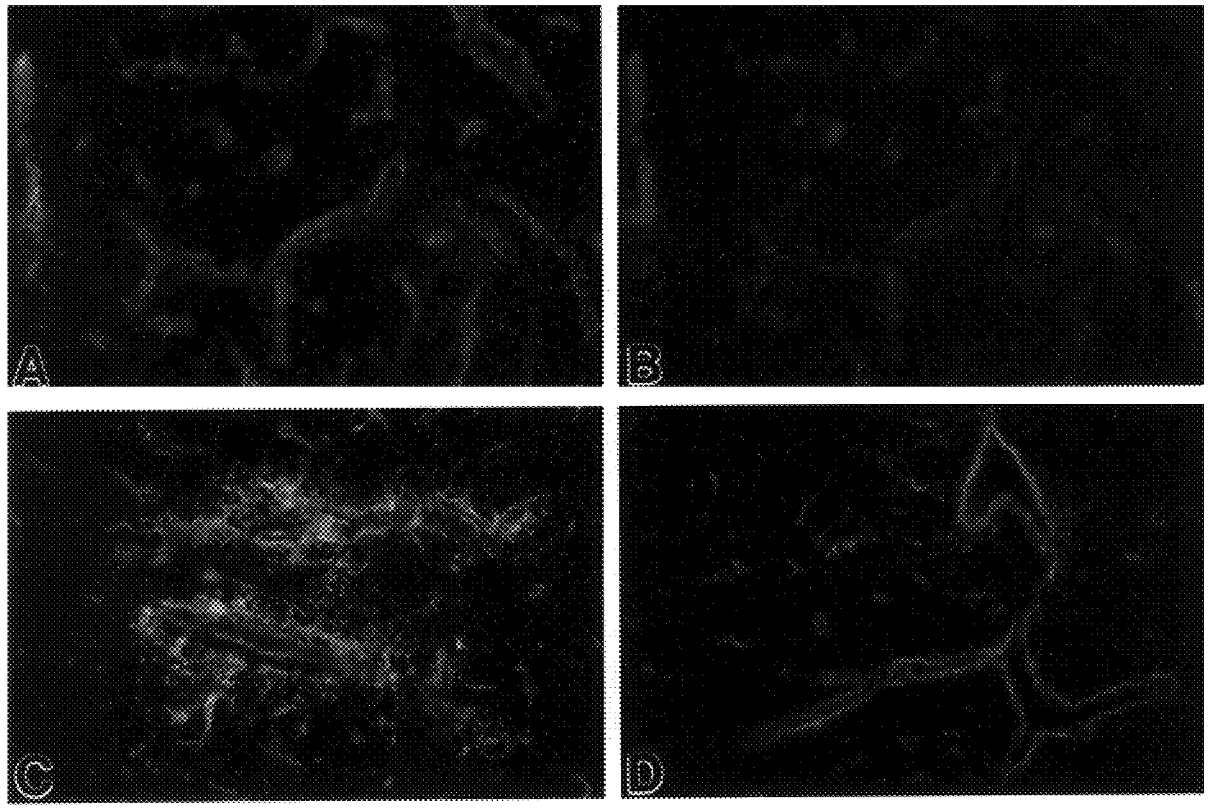

After 6 days of IGF-I and placebo treatment, in situ hybridization was used to compare relative levels of MBP mRNA in and around the EAE lesions in the two groups. Even though no demyelination was observed, MBP mRNA levels were higher in both groups than in sections from normal controls. Although not significant, the increase was greater in IGF-I- than in placebo-treated rats (FIG. 21).

2. Trial No. 2

In the second trial, when 11 days of treatment began the day after immunization, IGF-I-induced reductions in lesion numbers and areas were less striking but still significant at the P<0.05 level (data not shown). Other parameters were not quantitated but examination of immunostained sections indicated that lesions in IGF-I-treated rats also had fewer CD4+T cells and fewer ED1+ macrophages than those found in placebo-treated rats.

3. Trial No. 3

No results were obtained from Trial No. 3 due to the death of all 26 animals.

4. Summary of Results

The results indicate that IGF-I treatment significantly reduces clinical deficits and both the numbers and areas of immune-mediated inflammatory lesions in an EAE model that lacks changes associated with demyelination. IGF-I-induced reductions in lesion size and number were due to decreases in effector components of the immune response, namely, CD4+ T cells, α/β TCR+ cells and macrophages. IGF-I treatment also changed the distribution of macrophages; they remained localized perivascularly and were not as widely dispersed in white and grey matter as they were in sections of placebo-treated rats. Even though demyelination was not observed, MBP mRNA expression was slightly increased in and around lesions of both IGF-I- and placebo-treated rats, indicating mild but definite oligodendroglial dysfunction in this EAE model.

When IGF-I treatment was started 3 days before clinical symptoms appeared, clinical deficits, weight loss and lesion severity were reduced significantly but not prevented, suggesting that IGF-I did not have major effects of the induction of the immune response in this EAE model.

EXAMPLE 4

IGF-I-treatment-induced changes in blood-brain barrier-localized glucose transporter enzyme-1 (GT-1) during acute demyelinating EAE In studies of the ontogeny and cellular distribution of brain glucose transporter gene expression, it has been shown that glucose transporter-1 (GT-1) mRNA is abundant postnatally in brain and spinal cord vascular endothelium and adjacent glial (astrocyte) components of the blood-brain barrier (BBB)(Lee & Bondy, Mol. Cell. Neurosci. 3:305–314, 1992). Further studies have shown that during ischemic injury, GT-1 expression is upregulated within 1 hour throughout the forebrain (Lee and Bondy, Endocrinol., 133:2540–2544, 1993). Subsequently, GT-1 expression becomes localized to the ischemic hemisphere. This injury-induced upregulation was thought to represent a defensive response aimed at restoring energy stores and promoting functional recovery.

The effects of IGF-I treatment during EAE on BBB properties are reported in this example.

Acute demyelinating EAE was induced in Lewis rats as described generally in Example 2. Rats were treated with placebo or IGF-I (100 micrograms/kg) s.c. or i.v. every 12 hr starting on day 12 at the onset of clinical symptoms, and were continued for 8 days. Results for s.c. and i.v. treatments were the same and, therefore, were combined.

In and around demyelinating lesions found in placebo-treated rats, relative levels of GT-1 mRNA were strongly upregulated in endothelial cells and adjacent astrocytes (FIGS. 22–25), a pathological BBB injury response resembling that described in ischemia by Lee and Bondy (Endocrinol., 133:2540–2544, 1993). In contrast, relative mRNA levels of GT-1 in lesions of rats treated with IGF-I (200 micrograms/kg/day, s.c. or i.v.) were similar to those seen in corresponding areas of normal rat CNS (FIGS. 22–25).

The above is a new, unexpected, important effect of IGF-I treatment and adds significantly to the above evidence that IGF-I treatment reduces pathological changes in the BBB during demyelinating lesion development in EAE. Because the lesions in acute demyelinating EAE resemble those seen during active demyelination in MS, IGF-I treatment should also reduce early pathological changes in the BBB during MS, thereby reducing progression of inflammatory lesions, decreasing demyelination, and promoting functional recovery.

EXAMPLE 5

IGF-I-treatment during the first attack of chronic EAE also reduces clinical deficits and lesion severity during relapses Chronic relapsing EAE was induced by injecting 3×10⁷ MBP-specific T cells i.v. into 59 female SJL/J mice divided randomly into 4 groups. From day 7–16, two groups of mice received daily s.c. injections of IGF-I (0.6 mg/kg/day). The other two groups were controls and received daily s.c. placebo injections of 0.05 ml of IGF-I vehicle.

Figure 26:
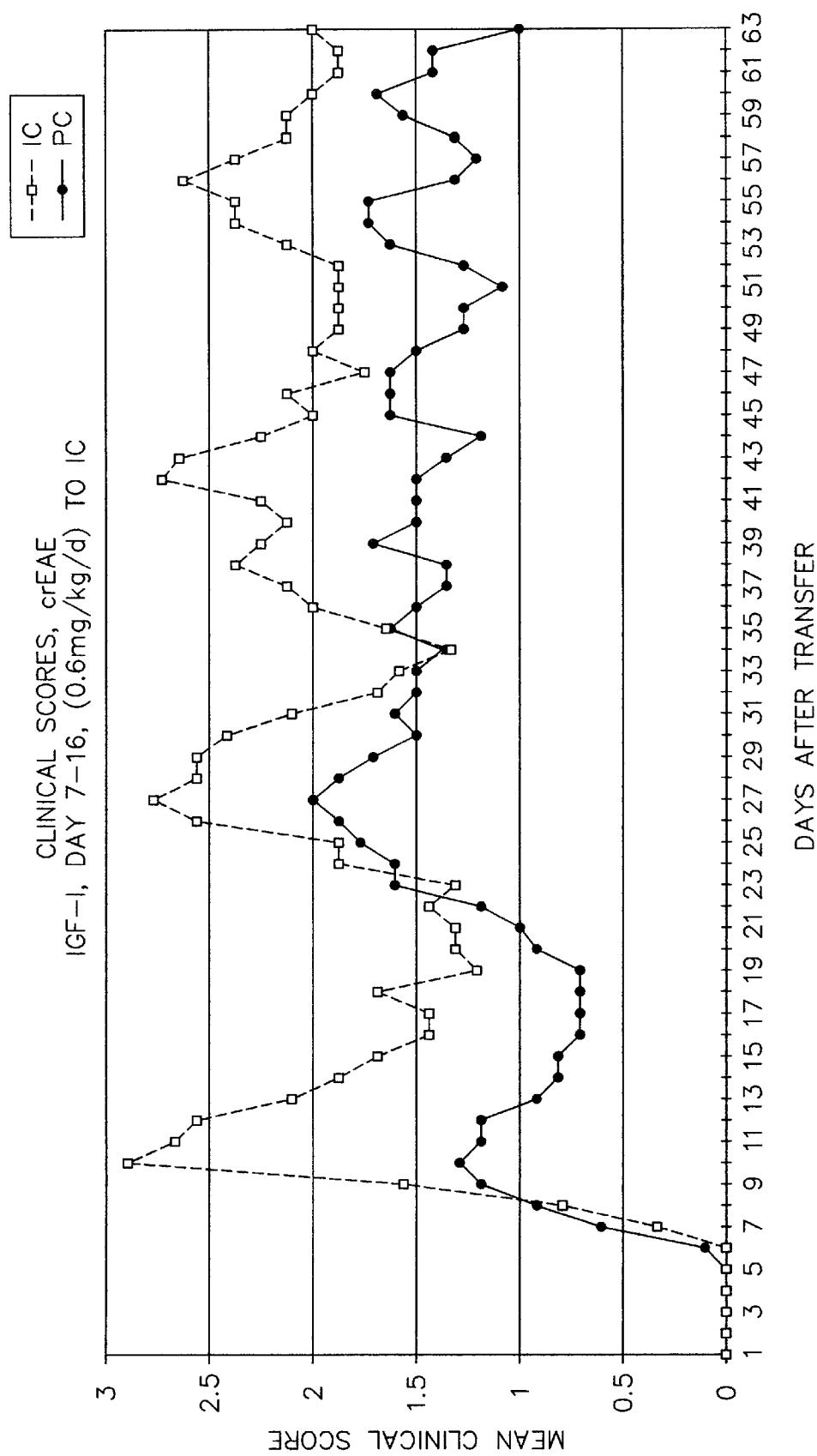
Figure 27:
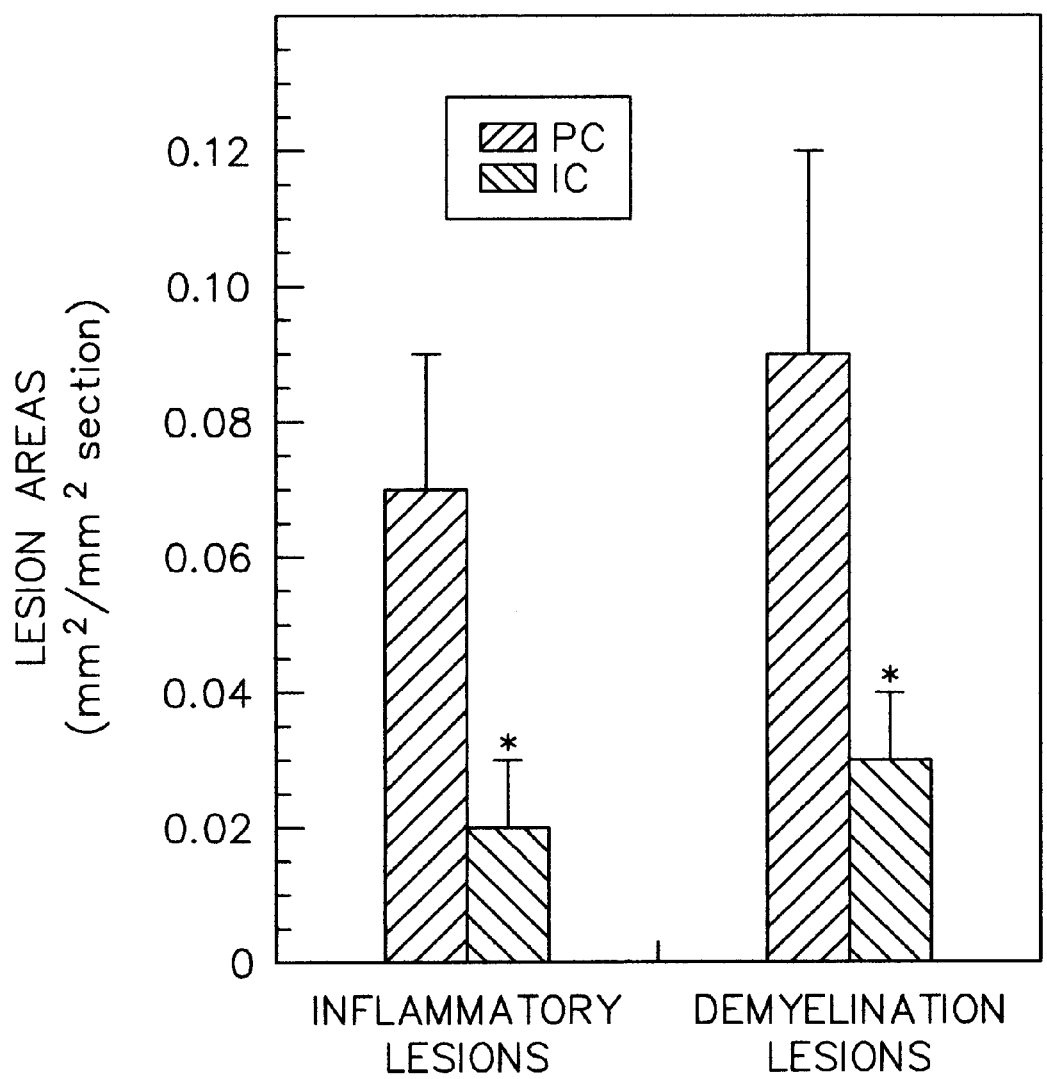

Three attacks of EAE were observed in placebo-treated mice. Maximum mean clinical scores (range 0=normal to 5=moribund) were 2.9 on day 10, and about 2.7 on days 27 and 42. IGF-I treatment from day 7–16 of the first attack reduce the maximum mean clinical score to 1.3 on day 10, significantly lower than the peak (2.9 on day 10) observed after placebo treatment (see FIG. 26). During the relapses which occurred after IGF-1 treatment stopped, the maximum mean clinical scores were only 2.0 (day 27) and 1.7 (day 42), both less than those observed after placebo treatment. In sections of brain, brainstem and spinal cord from IGF-I-treated mice, the inflammatory and demyelinative lesions were fewer in number and smaller in area than those from placebo-treated mice (see FIG. 27).

Thus, early treatment of chronic relapsing EAE with IGF-I not only significantly reduced the severity of the first attack but also decreased clinical deficits observed during two subsequent relapses. Chronic relapsing EAE is a useful model to test candidate therapies for MS because of the similarities in clinical course, blood-brain barrier defects, and immune-mediated demyelinating lesions. Therefore, the above findings indicate that IGF-I should be useful in treating relapsing remitting MS.

While the invention has been described and illustrated herein by reference to various specific material, procedures and examples, it is understood that the invention is not restricted to the particular materials, combinations of materials, and procedures selected for that purpose. Numerous variations of such details can be implied and will be appreciated by those skilled in the art.

All references unless otherwise noted herein, are hereby incorporated by reference.

We claim:

1. A method for reducing the severity of perivascular lesions comprising treating a patient in need thereof by administration of a therapeutically effective amount of IGF-I to said patient.

2. A method according to claim 1, wherein the formation of one or more new lesions is prevented.

3. A method according to claim 1, wherein the formation of one or more recurrent lesions is prevented.

4. A method according to claim 1, wherein the occurrence of one or more enlarging lesions is prevented.

5. A method according to claim 1, wherein the IGF-I is administered in a dose of about 1.0 nanogram to about 1.0 gram/kg body weight.

6. A method for promoting the healing of perivascular lesions comprising treating a patient in need thereof by administration of a therapeutically effective amount of IGF-I to said patient.

7. A method according to claim 6, wherein the promotion of the healing of said lesions is assessed based upon determination of a BOD differential score.

8. A method according to claim 6, wherein the IGF-I is administered in a dose of about 1.0 nanogram to about 1.0 gram/kg body weight.

9. The method of claim 1 wherein said perivascular lesions result in myelin injury to the central nervous system.

10. The method of claim 1 wherein said perivascular lesions result from the disease multiple sclerosis.

11. The method of claim 10 wherein said multiple sclerosis is selected from the group consisting of acute multiple sclerosis, relapsing-remitting multiple sclerosis, primary-progressive multiple sclerosis, and secondary-progressive multiple sclerosis.

12. The method of claim 11 wherein said multiple sclerosis is relapsing-remitting multiple sclerosis.

13. The method of claim 6 wherein said perivascular lesions result in myelin injury to the central nervous system.

14. The method of claim 6 wherein said perivascular lesions result from the disease multiple sclerosis.

15. The method of claim 14 wherein said multiple sclerosis is selected from the group consisting of acute multiple sclerosis, relapsing-remitting multiple sclerosis, primary-progressive multiple sclerosis, and secondary-progressive multiple sclerosis.

16. The method of claim 15 wherein said multiple sclerosis is relapsing-remitting multiple sclerosis.

* * * * *

UNITED STATES PATENT AND TRADEMARK OFFICE
CERTIFICATE OF CORRECTION

PATENT NO. : 5,965,531
DATED : Oct. 12, 1999
INVENTOR(S) : Webster, et al.

It is certified that error appears in the above-indentified patent and that said Letters Patent is hereby corrected as shown below:

Column 1, Line 7:

Delete "which claims the benefit of" and substitute -- and from -- therefor.

Column 7, Line 18:

Delete every occurrence of " $<$ " and substitute -- $\leq$ -- therefor.

Column 7, Line 21:

Delete " $<$ " and substitute -- $\leq$ -- therefor.

Column 8, Line 60:

Delete "reduces" and substitute -- reduce -- therefor.

Signed and Sealed this

Eleventh Day of July, 2000

Attest:

Q. TODD DICKINSON

Attesting Officer    Director of Patents and Trademarks